US005688767A

United States Patent [19]
Hancock et al.

[11] Patent Number: 5,688,767
[45] Date of Patent: Nov. 18, 1997

[54] TREATMENT OF ENDOTOXIN-ASSOCIATED DISORDERS WITH CATIONIC PEPTIDES

[75] Inventors: Robert E. W. Hancock, Vancouver; Kevin L. Piers, Red Deer, both of Canada; Melissa H. Brown, Canterbury, Australia; Niamh Kelly, Vancouver, Canada

[73] Assignee: University of British Columbia, Vancouver, Canada

[21] Appl. No.: 614,516

[22] Filed: Mar. 13, 1996

Related U.S. Application Data

[60] Division of Ser. No. 405,234, Mar. 13, 1995, which is a continuation-in-part of Ser. No. 110,502, Aug. 20, 1993, abandoned, which is a continuation-in-part of Ser. No. 933,492, Aug. 21, 1992, abandoned.

[51] Int. Cl.$^6$ .................................................... A61K 38/16
[52] U.S. Cl. ............................. 514/12; 435/69.7; 435/252.1
[58] Field of Search ......................... 514/12; 435/69.7, 435/252.1

[56] References Cited

FOREIGN PATENT DOCUMENTS

WO 94/04688  3/1994  WIPO.

*Primary Examiner*—Charles L. Patterson, Jr
*Attorney, Agent, or Firm*—Fish & Richardson, P.C.

[57] ABSTRACT

A method for the microbial production of a cationic peptide having anti-microbial activity is provided, wherein the cationic peptide is first produced as a fusion protein having an anionic portion for suppressing the antimicrobial activity of the cationic portion. A novel cationic peptide having anti-microbial activity and LPS-binding activity is also provided. Such peptides are useful for suppressing the growth of bacteria and for the treatment of endotoxemia-associated disorders.

6 Claims, 19 Drawing Sheets

CEME and derivatives

CEME and derivatives with Factor Xa

HNP-1 and derivatives

HNP-1 with Met residue

Pre Pro cassette

Pre Pro HNP-1 cassette

HNP-1  A C Y C R I P A C I A G E R R Y G T C I Y Q G R L W A F C C

CEME   K W K L F K K I G I G A V L K V L T T G L P A L I S

CEMA   K W K L F K K I G I G A V L K V L T T G L P A L K L T K

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..104

( x i ) SEQUENCE DESCRIPTION: SEQ ID NO:1:

```
CGGGGATCCG  CATATGAAAT  GGAAACTGTT  CAAGAAGATC  GGCATCGGCG  CCGTGCTGAA         60

AGTGCTGACC  ACCGGTCTGC  CGGCGCTGAT  CAGCTAACTA  AGTA                         104
```

( 2 ) INFORMATION FOR SEQ ID NO:2:

( i ) SEQUENCE CHARACTERISTICS:
        ( A ) LENGTH: 112 base pairs
        ( B ) TYPE: nucleic acid
        ( C ) STRANDEDNESS: single
        ( D ) TOPOLOGY: linear (i i) MOLECULE TYPE: DNA (genomic)

(i x) FEATURE:
    (A) NAME/KEY: CDS
    (B) LOCATION: 3..112

(x i) SEQUENCE DESCRIPTION: SEQ ID NO:2:

```
AGCTTACTTA GTTAGCTGAT CAGCGCCGGC AGACCGGTGG TCAGCACTTT CAGCACGGCG    60
CCGATGCCGA TCTTCTTGAA CAGTTTCCAT TTCATATGCG GATCCCCGCA TG          112
```

(2) INFORMATION FOR SEQ ID NO:3:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (i x) FEATURE:
        (A) NAME/KEY: CDS
        (B) LOCATION: 2..81

(x i) SEQUENCE DESCRIPTION: SEQ ID NO:3:

```
GGGAGCTCCT AACTAACTAA GGAGGAGACA TATGAAACAA AGCACTATTG CACTGGCACT    60
CTTACCGTTA CTGTTTACCC C                                              81
```

(2) INFORMATION FOR SEQ ID NO:4:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 2..55

(x i) SEQUENCE DESCRIPTION: SEQ ID NO:4:

```
CCAGTGCAAT AGTGCTTTGT TTCATATGTC TCCTCCTTAG TTAGTTAGGA GCTCC    55
```

(2) INFORMATION FOR SEQ ID NO:5:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (i i) MOLECULE TYPE: DNA (genomic)

(i x) FEATURE:
        (A) NAME/KEY: CDS
        (B) LOCATION: 2..65

(x i) SEQUENCE DESCRIPTION: SEQ ID NO:5:

```
TGTGACAAAA GCCGCATGCT ACTGCCGTAT ACCGGCCTGC ATCGCGGGCG AACGTCGTTA    60
CGGTA                                                                65
```

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: single
        (D) TOPOLOGY: linear ( i i ) MOLECULE TYPE: DNA (genomic)

( i x ) FEATURE:
    ( A ) NAME/KEY: CDS
    ( B ) LOCATION: 3..64

( x i ) SEQUENCE DESCRIPTION: SEQ ID NO:6:

```
CAGGCCGGTA TACGGCAGTA GCATGCGGCT TTTGTCACAG GGGTAAACAG TAACGGTAAG    60

AGTG                                                                 64
```

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 3..50

( x i ) SEQUENCE DESCRIPTION: SEQ ID NO:7:

```
CCTGCATCTA CCAGGGCCCT CTGTGGGCGT TCTGCTGCTA AAAGCTTCGC               50
```

( 2 ) INFORMATION FOR SEQ ID NO:8:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..76

( x i ) SEQUENCE DESCRIPTION: SEQ ID NO:8:

```
GCGAAGCTTT TAGCAGCAGA ACGCCCACAG ACGGCCCTGG TAGATGCAGG TACCGTAACG    60

ACGTTCGCCC GCGATG                                                    76
```

( 2 ) INFORMATION FOR SEQ ID NO:9:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..110

( x i ) SEQUENCE DESCRIPTION: SEQ ID NO:9:

```
CCATATGAGG ACCCTCGCCA TCCTTGCTGC CATTCTCCTG GTGGCCCTGC AGGCCCAGGC    60

TGAGCCACTC CAGGCAAGAG CTGATGAGGT TGCAGCAGCC CCGGAGCAGA              110
```

( 2 ) INFORMATION FOR SEQ ID NO:10:

( i ) SEQUENCE CHARACTERISTICS:
        ( A ) LENGTH: 91 base pairs
        ( B ) TYPE: nucleic acid
        ( C ) STRANDEDNESS: single (D) TOPOLOGY: linear (i i) MOLECULE TYPE: DNA (genomic)

(i x) FEATURE:
    (A) NAME/KEY: CDS
    (B) LOCATION: 3..91

(x i) SEQUENCE DESCRIPTION: SEQ ID NO:10:

```
TTGCAGCTGA CATCCAGAA GTGGTTGTTT CCCTTGCATG GGACGAAACG TTGGCTCCAA      60
AGCATCCAGG CTCAAGGAAA AACATGGCAT G                                    91
```

(2) INFORMATION FOR SEQ ID NO:11:

(i) SEQUENCE CHARACTERISTICS:
    (A) LENGTH: 109 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 2..109

(x i) SEQUENCE DESCRIPTION: SEQ ID NO:11:

```
CCATGTTTTT CCTTGAGCCT GGATGCTTTG GAGCCAAGCT TTCGTCCCAT GCAAGGGAAA      60
CAACCACTTC TGGGATGTCA GCTGCAATCT GCTCCGGGGC TGCTGCAAC                 109
```

(2) INFORMATION FOR SEQ ID NO:12:

(i) SEQUENCE CHARACTERISTICS:
    (A) LENGTH: 92 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 1..92

(x i) SEQUENCE DESCRIPTION: SEQ ID NO:12:

```
CTCATCAGCT CTTGCCTGGA GTGGCTCAGC CTGGGCCTGC AGGGCCAGCA GGAGAATGGC      60
AGCAAGGATG GCGAGGGTCC TCATATGGCA TG                                   92
```

(2) INFORMATION FOR SEQ ID NO:13:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 1..12

(x i) SEQUENCE DESCRIPTION: SEQ ID NO:13:

```
AGCTTGTCGA CA                                                         12
```

(2) INFORMATION FOR SEQ ID NO:14:

(i) SEQUENCE CHARACTERISTICS:
    (A) LENGTH: 24 base pairs (B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 2..24

(x i) SEQUENCE DESCRIPTION: SEQ ID NO:14:

CGTCGACATC GAAGGTCGTG CATG 24

(2) INFORMATION FOR SEQ ID NO:15:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 2..24

(x i) SEQUENCE DESCRIPTION: SEQ ID NO:15:

CACGACCTTC GATGTCGACG CATG 24

(2) INFORMATION FOR SEQ ID NO:16:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 1..12

(x i) SEQUENCE DESCRIPTION: SEQ ID NO:16:

AATTCGGATC CG 12

(2) INFORMATION FOR SEQ ID NO:17:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 1..15

(x i) SEQUENCE DESCRIPTION: SEQ ID NO:17:

CGGATCCATG GCATG 15

(2) INFORMATION FOR SEQ ID NO:18:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: DNA (genomic)

(i x) FEATURE:
    (A) NAME/KEY: CDS
    (B) LOCATION: 2..15

(x i) SEQUENCE DESCRIPTION: SEQ ID NO:18:

CCATGGATCC GCATG                                                       15

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 2..12

(x i) SEQUENCE DESCRIPTION: SEQ ID NO:19:

TATGGGATCC CA                                                          12

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..23

(x i) SEQUENCE DESCRIPTION: SEQ ID NO:20:

CCAAAATCGG ATCTGATCGA AGG                                 23

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..20

(x i) SEQUENCE DESCRIPTION: SEQ ID NO:21:

CAGATCGTCA GTCAGTCACG                                       20

(2) INFORMATION FOR SEQ ID NO:22:

(i) SEQUENCE CHARACTERISTICS:
        (A) LENGTH: 30 amino acids
        (B) TYPE: amino acid
        (C) STRANDEDNESS: single
        (D) TOPOLOGY: linear (i i) MOLECULE TYPE: protein (i x) FEATURE:
        (A) NAME/KEY: Protein (B) LOCATION: 1..30

(xi) SEQUENCE DESCRIPTION: SEQ ID NO:22:

Ala Cys Tyr Cys Arg Ile Pro Ala Cys Ile Ala Gly Glu Arg Arg Tyr
1               5                   10                  15
Gly Thr Cys Ile Tyr Gln Gly Arg Leu Trp Ala Phe Cys Cys
            20              25                  30

(2) INFORMATION FOR SEQ ID NO:23:

(i) SEQUENCE CHARACTERISTICS:
      (A) LENGTH: 26 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..26

(xi) SEQUENCE DESCRIPTION: SEQ ID NO:23:

Lys Trp Lys Leu Phe Lys Lys Ile Gly Ile Gly Ala Val Leu Lys Val
1               5                   10                  15
Leu Thr Thr Gly Leu Pro Ala Leu Ile Ser
            20              25

(2) INFORMATION FOR SEQ ID NO:24:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (B) CLONE: CEMA (ix) FEATURE:
      (A) NAME/KEY: Peptide
      (B) LOCATION: 1..28

(xi) SEQUENCE DESCRIPTION: SEQ ID NO:24:

Lys Trp Lys Leu Phe Lys Lys Ile Gly Ile Gly Ala Val Leu Lys Val
1               5                   10                  15
Leu Thr Thr Gly Leu Pro Ala Leu Lys Leu Thr Lys
            20              25

(2) INFORMATION FOR SEQ ID NO:25:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: CEMA variant primer (ix) FEATURE:
      (A) NAME/KEY: CDS
      (B) LOCATION: 1..27

(xi) SEQUENCE DESCRIPTION: SEQ ID NO:25:

GGCGCTGAAG CTAACTAAGT AAGCTTG                                   27

(2) INFORMATION FOR SEQ ID NO:26:

(i) SEQUENCE CHARACTERISTICS:
　　　　(A) LENGTH: 31 base pairs
　　　　(B) TYPE: nucleic acid
　　　　(C) STRANDEDNESS: single
　　　　(D) TOPOLOGY: linear (ii) MOLECULE TYPE: DNA (genomic)

(vii) IMMEDIATE SOURCE:
　　　　(B) CLONE: CEMA variant primer (ix) FEATURE:
　　　　(A) NAME/KEY: CDS
　　　　(B) LOCATION: 1..31

(xi) SEQUENCE DESCRIPTION: SEQ ID NO:26:

AATTCAAGCT TACTTAGTTA GCTTCAGCGC C　　　　　　　　　　31

TREATMENT OF ENDOTOXIN-ASSOCIATED DISORDERS WITH CATIONIC PEPTIDES

This application is a continuation-in-part of application Ser. No. 08/405,234, filed Mar. 13, 1995, which is a continuation-in-part of application Ser. No. 08/110,502, filed Aug. 20, 1993, now abandoned which is a continuation-in-part of application Ser. No. 07/933,492, filed Aug. 21, 1992, now abandoned.

BACKGROUND OF THE INVENTION

1. Field of the Invention

The invention relates to recombinant vector systems and more specifically to the use of these systems for production of antimicrobial cationic peptides.

2. Description of Related Art

In 1981, the self-promoted uptake hypothesis was first proposed to explain the mechanism of action of polycationic antibiotics in *Pseudomonas aeruginosa*. According to this hypothesis, polycations interact with sites on the outer membranes of Gram-negative bacteria at which divalent cations cross-bridge adjacent lipopolysaccharide molecules. Due to their higher affinity for these sites, polycations displace the divalent cations and, since the polycations are bulkier than the divalent cations, cause structural perturbations in the outer membrane. These perturbations result in increased outer membrane permeability to compounds such as the β-lactam antibiotic nitrocefin, the eukaryotic non-specific defense protein lysozyme and to hydrophobic substances. By analogy, molecules accessing this pathway are proposed to promote their own uptake.

It has been clearly demonstrated that the outer membranes of Gram-negative bacteria are semipermeable molecular "sieves" which restrict access of antibiotics and host defense molecules to their targets within the bacterial cell. Thus, cations and polycations which access the self-promoted uptake system are, by virtue of their ability to interact with and break down the outer membrane permeability barrier, capable of increasing the susceptibility of Gram-negative pathogenic bacteria to antibiotics and host defense molecules. Hancock and Wong demonstrated that a broad range of such compounds could overcome the permeability barrier and coined the name "permeabilizers" to describe them (Hancock and Wong, *Antimicrob. Agents Chemother.*, 26:48, 1984). While self-promoted uptake and permeabilizers were first described for *P. aeruginosa*, they have now been described for a variety of Gram-negative bacteria.

Over the past decade, non-specific defense molecules have been described in many animals, including insects and humans. One subset of these molecules have in common the following features: (a) they are small peptides, usually 15–35 amino acids in length, (b) they contain 4 or more positively charged amino acid residues, either lysines or arginines, and (c) they are found in high abundance in the organisms from which they derive. Several of these molecules have been isolated, amino acid sequenced and described in the patent literature (e.g., cecropins: WO8900199, WO 8805826, WO8604356, WO 8805826; defensins: EP 193351, EP 85250, EP 162161, US 4659692, WO 8911291). However, only limited mounts of these peptides can be isolated from the host species. For example, Sawyer, et al., (*Infect. Immun.* 56:693, 1988) isolated 100–200 mg of rabbit neutrophil defensins 1 and 2 from $10^9$ primed peritoneal neutrophils or lipopolysaccharide-elicited alveolar macrophages (i.e., the numbers present in a whole animal).

Systemic disease associated with the presence of pathogenic microorganisms or their toxins in the blood (i.e. septicemia) is a leading cause of death where it accounts for an estimated $5–10 billion in annual health care expenditures. Gram negative bacteria are often associated with this disease and their pathogenesis is in pan related to the release of an outer membrane component, endotoxin. Endotoxin is classically a lipopolysaccharide (LPS)-protein complex, although the endotoxic activity is entirely contained within the lipid A portion of LPS. Symptoms associated with the presence of circulating endotoxin include fever, hypertension, and, under more extreme cases, endotoxic shock.

It is known that many antibiotics stimulate the release of endotoxin, and thus stimulate the occurrence of such symptoms. Indeed, even those patients cured of bacterial infection are at immediate risk from endotoxic shock.

The physiological mechanism whereby endotoxin exerts its affects on man involves the release of cytokines, of which tumor necrosis factor (TNF) appears to be the most significant one. Experimental data has demonstrated that (i) circulating TNF can be detected in animals that have had administered lethal doses of endotoxin (Beutler, et al., *J. Immunol.*, 135:3972, 1985), (ii) injection of TNF into experimental animals recreates the symptoms of endotoxin injection (Beutler, et al., supra; Tracey, et al., *Nature*, 330:662, 1987; Beutler, et al., *Science*, 229:869, 1985) and (iii) treatment of laboratory animals with anti-TNF reverses the lethal effects of endotoxin (Beutler, et at., supra, *Science*; Mathinson, et al., *J. Clin. Invest.*, 88:1925, 1988). This latter observation led immediately to the notion that anti-TNF antibody might offer a therapeutic regime for lethal endotoxic shock. Accordingly, an anti-TNF monoclonal antibody was recently tested in a large phase II/III clinical trial (Wherry, et al., *Chest.*, 104:3S, 1993). Unfortunately, the trial indicated that anti-TNF was not a valid treatment when administered to patients presenting with bacteremia and organ dysfunction and, furthermore, failed to demonstrate any proven benefit even in the subgroup of patients presenting with endotoxic shock.

SUMMARY OF THE INVENTION

This invention provides a novel method for producing a cationic peptide by recombinantly producing a fusion peptide which is composed of the cationic peptide and an anionic peptide. The fusion peptide can preferably later be cleaved to release the cationic peptide, which can then be purified. Numerous polycationic peptide structures from nature have been reported and have been either demonstrated or hypothesized to act as outer membrane permeabilizers. The cationic peptides produced by the method of the invention can be used synergistically with classical antibiotics to break down the outer membrane permeability barrier, which is one of the major limiting factors in antibiotic activity against Gram-negative bacteria. Such permeabilizers demonstrate an enormous range of amino acid sequences, lengths, and predicted 3-dimensional structures. Until the present invention, no general method had been described that would allow the production of polycationic peptides in meaningful quantities in bacteria.

In another embodiment, the invention provides a novel cationic peptide which is a fusion between selected cecropia and melittin sequences with additional modifications. This novel peptide possesses enhanced anti-bacterial activity as compared with previously described cationic peptides.

In yet another embodiment, the invention provides a method of inhibiting an endotoxemia or sepsis associated disorder comprising administering to a subject with the disorder a therapeutically effective amount of a cationic peptide. Preferably, the peptide is CEME or CEMA (SEQ ID NO: 23 and 24, respectively) of the invention.

BRIEF DESCRIPTION OF THE DRAWINGS

FIG. 3 shows the amino acid sequences of human neutrophil peptide-1 (HNP-1 ), the cecropia A/melittin hybrid peptide (CEME) and (CEMA). Positively charged amino acids are in bold.

DETAILED DESCRIPTION OF THE INVENTION

Figure 1B:
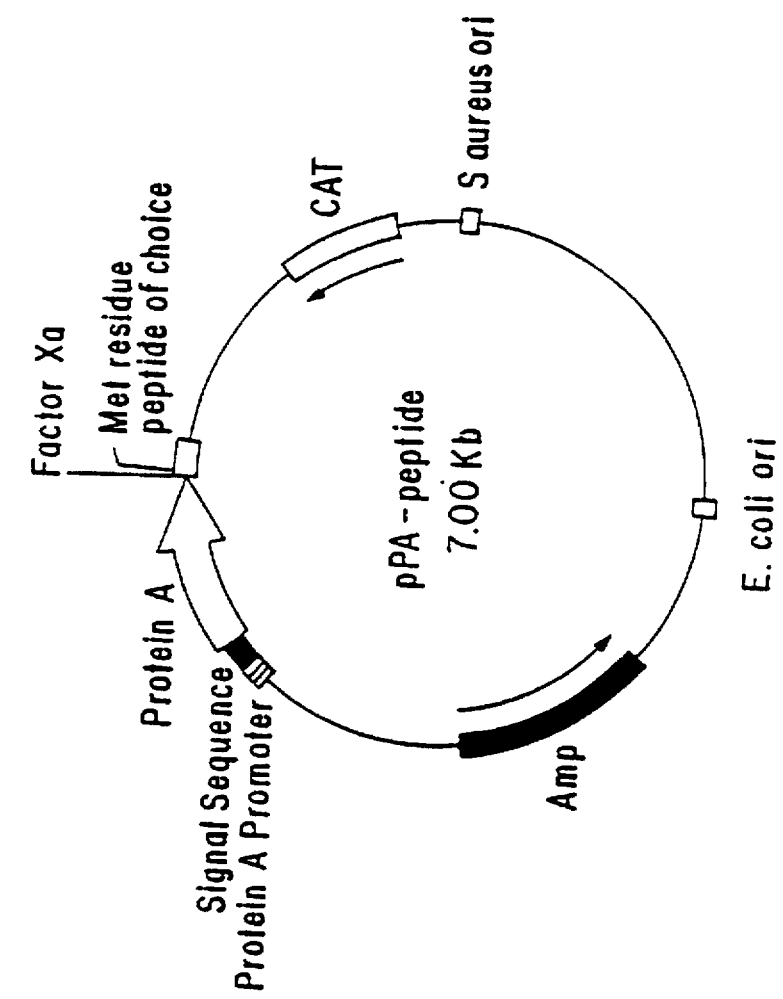
FIG. 1 shows a schematic representation of the plasmids used in the invention; A, pGST-peptide; B, pPA-peptide; C, pEZZ-peptide; D, pOprF-peptide.
Figure 1A:
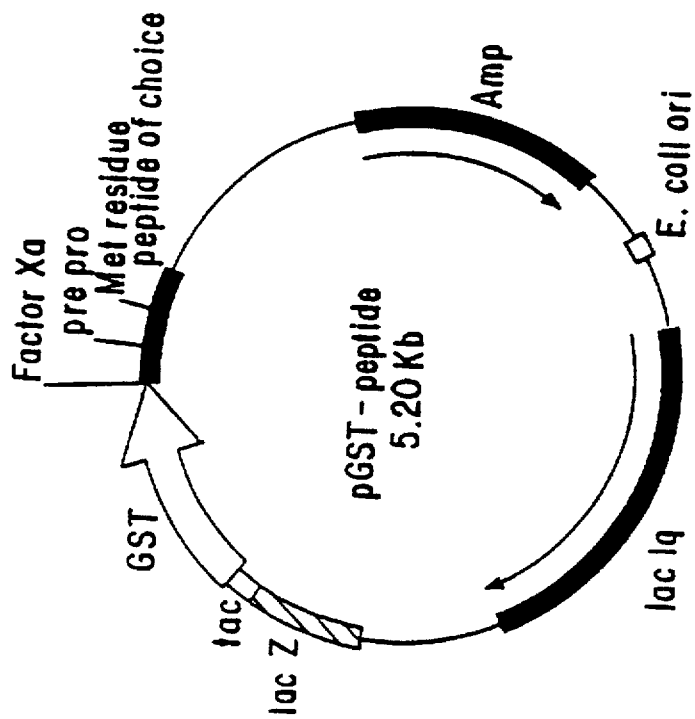

The method of this invention provides production of fusion proteins comprising an anionic peptide and an antimicrobial cationic peptide. Initially, when sequences encoding cationic peptides were placed into expression vectors without an amino terminal sequence encoding an anionic carrier peptide or with just a signal sequence encoding region or pre-pro defensin encoding region (i.e., the regions which result in export in bacteria or eukaryotes, respectively), no peptide was observed despite the presence of measurable mRNA levels in the cytoplasm. This finding indicated that some intracytoplasmic mechanism might somehow be preventing the translation of the mRNA or degrading the translation product. This problem has been solved in the present invention by fusing an anionic carrier peptide to the cationic peptide such that stabilization occurs and breakdown by bacterial proteases is avoided.

As used herein, the term "cationic peptide" refers to a sequence of amino acids from about 5 to about 50 amino acids in length and preferably from about 15 to about 35 amino acids in length. A peptide is "cationic" if it possesses sufficient positively charged amino acids that has a pKa greater than 9.0. Typically, at least four of the amino acid residues of the cationic peptide can be positively charged, for example, lysine or arginine. "Positively charged" refers to the side chains of the amino acid residues which have a net positive charge at pH 7.0. Examples of naturally occurring cationic peptides which can be recombinantly produced according to the invention include defensins, magainins, melittin, and cecropins, and analogs thereof.

According to the method of the present invention, the fusion peptide comprises a "carrier peptide" which is encoded by a nucleotide sequence present in the expression vector. The "carrier peptide" is preferably located at the amino-terminal end of the fusion peptide sequence. The carrier peptide is sufficiently anionic such that the positive charge associated with the cationic peptide is overcome. As a result, the fusion peptide has a net charge which is essentially neutral or even negative. The anionic carrier peptide may be derived from naturally-occurring proteins or can be entirely artificial. Functionally, the carrier peptide stabilizes the cationic peptide and protects it from bacterial proteases. The carrier peptide of the method of the invention may further function to transport the fusion peptide to inclusion bodies, the periplasm, the outer membrane or, preferably, the external environment. Categories of carrier peptide which can be utilized according to the invention include anionic pre-pro peptides and anionic outer membrane peptides. Carrier peptides of the invention specifically include, but are not limited to glutathione-S-transferase (GST) (Smith et al., *Proc. Natl. Acad. Sci. USA*, 83:8703 (1986)), protein A from *Staphylococcus aureus* (Nilsson, et al., EMBO 4:1075 (1985)), two synthetic IgG-binding domains (ZZ) of protein A (Löwenadler, et al., *Gene*, 58:87, 1987) and outer membrane protein F from *Pseudomonas aeruginosa* (Duchene, et al., *J. Bacteriol*, 170:155, 1988). The invention is not limited to the use of these peptides as carriers; others with similar properties as the carriers described herein are known to those skilled in the art, or can be readily ascertained without undue experimentation.

Techniques for the isolation and purification of the microbially expressed polypeptides of the invention may be by any conventional means such as, for example, preparative chromatographic separations and immunological separations such as those involving the use of monoclonal or polyclonal antibody. The use of glutathione-S-transferase (GST) as the carrier protein, allows purification with a glutathione agarose affinity column. When either Protein A or the ZZ domain from *Staphylococcus aureus* is used as the carrier protein, single step purification can be done using an IgG-sepharose affinity column, for example. Use of pOprF-peptide, the N-terminal half of the *P. aeruginosa* outer membrane protein F, is advantageous, since it is the prominent protein band found in outer membrane preparations and therefore can also be purified easily. Alternatively, the fusion peptides can be isolated by use of reagents specifically reactive with the cationic peptide portion of the fusion peptide. Along these lines, monoclonal antibodies which bind an epitope present in the cationic peptide can be utilized, for example, by using standard solid phase affinity purification methodology.

In one embodiment of the invention, a signal sequence is included in the expression vector, specifically located adjacent to the N-terminal end of the carrier protein. The signal sequence allows the fusion protein to be directed toward the membrane. The signal sequence usually consists of a leader of from about 16 to about 29 amino acids, starting with two or three polar residues and continuing with a high content of hydrophobic amino acids; there is otherwise no detectable conservation of sequence known. While the vectors used as examples in the present invention use the protein A signal sequence of Staphylococcus or the OprF signal sequence in *Pseudomonas aeruginosa*, other signal sequences which provide the means for transport of the fusion protein to the cell membrane will be equally effective in carrying out the method of the invention. Such signal sequences are known to those of skill in the art.

According to the invention, it may be advantageous to include a "spacer DNA sequence" in the vectors used in the method of the invention. As used herein, "spacer DNA sequence" refers to any DNA sequence located between the carrier peptide DNA sequence and the cationic peptide DNA sequence of the fusion peptide vector. While not wanting to be bound by a particular theory, it is believed that the spacer DNA sequence, when translated, may create a "hinge-like" region which allows the negatively charged residues of the anionic carrier peptide and the positively charged residues of the subject cationic peptide to interact, thereby inhibiting the positive charge effect and associated detrimental phenomena, such as degradation by proteolytic enzymes.

In addition to stability, the spacer DNA sequence may provide a site for cleavage of the carrier peptide from the peptide after synthesis of the fusion peptide. For example, such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at the methionine or related codons. In addition, the fused product can be cleaved by insertion of a codon for tryptophan (clearable by o-iodosobenzoic acid) or glutamic acid (cleavable by Staphylococcus protease). Insertion of such spacer DNA sequences is not a requirement for the production of functional cationic peptides, however, specific sequences will enhance the stability of the fusion peptide. The pre-pro defensin sequence is negatively charged, therefore it is envisioned within the invention that other DNA sequences encoding negatively charged peptides could be used as spacer DNA sequences to stabilize the fusion peptide and prevent degradative events, such as bacterial proteolytic degradation. Spacer DNA sequences, such as the pre-pro defensin amino terminal sequences, are also efficient in the transport of fusion peptide to the outside of the host cell membrane.

In the present invention, the cationic sequences may be inserted into a recombinant "expression vector". The term "expression vector" refers to a plasmid, virus or other vehicle known in the art that has been manipulated by insertion or incorporation of cationic genetic sequences. Such expression vectors of the invention are preferably plasmids which contain a promoter sequence which facilitates the efficient transcription of the inserted genetic sequence in the host. The expression vector typically contains an origin of replication, a promoter, as well as specific genes which allow phenotypic selection of the transformed cells. For example, the expression of the fusion peptide of the invention can be placed under control of *E. coli* chromosomal DNA comprising a lactose or lac operon which mediates lactose utilization by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene.

Transformation of the host cell with the recombinant DNA may be carried out by conventional techniques well known to those skilled in the art. For example, where the host is prokaryotic, such as *E. coli*, competent cells which are capable of DNA uptake can be prepared from cells harvested after exponential growth and subsequently treated by the $CaCl_2$ method using procedures well known in the art. Alternatively, $Mg_2Cl$ or RbCI could be used.

In addition to conventional chemical methods of transformation, the plasmid vectors of the invention may be introduced into a host cell by physical means, such as by electroporation or micro injection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art.

DNA sequences encoding the cationic peptides can be expressed in vivo by DNA transfer into a suitable host cell. "Host cells" of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include *E. coli*, *S. aureus* and *P. aeruginosa*, although other Gram-negative and Gram-positive organisms known in the art can be utilized as long as the expression vectors contain an origin of replication to permit expression in the host.

The cationic peptide DNA sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of mRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived form reverse transcription of mRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carded out on cloned copies of the cDNA which have been denatured into a single stranded form (Jay, et al., *Nuc. Acid Res.*, 11:2 325, 1983).

The invention also provides an isolated peptide comprising Sequence ID No. 24, and conservative variations thereof. The peptide, CEMA, contains the first 18 amino acids of cecropia and the last 8 amino acids of melittin. CEMA has been altered by changing the carboxy terminal amino acid sequence of CEME to include two extra lysine residues. This modification unexpectedly created a sequence with two-fold improved antibiotic activity against many bacterial species as well as a substantially enhanced ability to permeabilize bacterial outer membranes and bind to lipopolysaccharide (LPS). Alternatively, other positively charged amino acids could be substituted for lysine, as long as their charge is positive at pH 7.0.

Minor modifications of the primary amino acid sequence of the peptide of the invention may result in peptides which have substantially equivalent activity as compared to the specific peptide described herein. Such modifications may be deliberate, as by site-directed mutagenesis, or may be spontaneous. All of the peptides produced by these modifications are included herein as long as the biological activity of the original peptide still exists. Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed.

The peptide of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides polynucleotides which encode the peptides of the invention. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code.

The invention also provides a method of inhibiting the growth of bacteria comprising contacting the bacteria with an inhibiting effective amount of the CEMA peptide of the invention. The term "contacting" refers to exposing the bacteria to CEMA so that CEMA can effectively inhibit, kill, or lyse bacteria, bind endotoxin (LPS), or permeabilize gram-negative bacterial outer membranes. Contacting may be in vitro, for example by adding CEMA to a bacterial culture to test for susceptibility of the bacteria to the peptide. Contacting may be in vivo, for example administering CEMA to a subject with a bacterial disorder, such as septic shock. "Inhibiting" or "inhibiting effective amount" refers to the amount of CEMA which is required to cause a bacteriostatic or bacteriocidal effect. Examples of bacteria which may be inhibited include *E. coli, P. aeruginosa, E. cloacae, S. typhimurium,* and *S. aureus.* The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art.

The peptide of the invention can be administered parenterally by injection or by gradual infusion over time. The peptide can be administered intravenously, intra peritoneally, intramuscularly, subcutaneously, intra activity, or transdermally. Preferred methods for delivery of the peptide include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, cheating agents, and inert gases and the like.

The invention provides a method of treating or ameliorating an immunopathological disorder such as endotoxemia or septic shock (sepsis), or one or more of the symptoms of sepsis comprising administering to a subject displaying symptoms of sepsis or at risk for developing sepsis, a therapeutically effective amount of cationic peptide. The term "ameliorate" refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli*, *Klebsiella* sp., *Pseudomonas aeruginosa*, *Serratia* sp., *Enterobacter* sp., *Proteus* sp., *Haemophilus influenza B*, *Neisseria meningitidis*. Patients at risk for sepsis include those suffering from burns, gunshot wounds, renal or hepatic failure, trauma, immunocompromised (HIV), hematopoietic neoplasias, multiple myeloma, Castleman's disease or cardiac myxoma.

The term "therapeutically effective amount" as used herein for treatment of endotoxemia refers to the amount of cationic peptide used is that of sufficient quantity to decrease the subject's response to LPS and decrease the symptoms of sepsis. The term "therapeutically effective" therefore includes that the amount of cationic peptide sufficient to prevent, and preferably reduce by at least 50%, and more preferably sufficient to reduce by 90%, a clinically significant increase in the plasma level of TNF. The dosage ranges for the administration of cationic peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of cationic peptide, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with an antibiotic in addition to the treatment with cationic peptide. Typical antibiotics include an amino glycoside, such as gentamicin or a beta-lactam such as penicillin, or cephalosporin. Therefore, a preferred therapeutic method of the invention includes administering a therapeutically effective amount of cationic peptide substantially simultaneously with administration of a bactericidal amount of an antibiotic. Preferably, administration of cationic peptide occurs within about 48 hours and preferably within about 2-8 hours, and most preferably, substantially concurrently with administration of the antibiotic.

In this respect, the bactericidal action of the cationic peptides of the invention and their ability to act cooperatively with other antibiotics in killing bacteria is particularly important. Indeed an important feature of cationic peptides is that they are shown here to neutralize LPS whereas most antibiotics induce LPS release from bacteria as part of the process of killing cells.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

The following examples are intended to illustrate but not limit the invention. While they are typical of those that might be used, other procedures known to those skilled in the art may alternatively be utilized.

EXAMPLE 1

Construction of pGST-peptide Plasmids

This plasmid was derived from pGEX-3X (Smith, et al., *Proc. Natl. Acad. Sci., U.S.A.*, 83:8703, 1986) using recombinant DNA technology. A 500 bp BclI-BamHI fragment from pGEX-3X that included the Factor X cleavage site and part of the glutathione-S-transferase gene was isolated. This fragment was subjected to 35 cycles of PCR (94° C. for 1 minute, 50° C. for 1 minute, 72° C. for 1 minute) in an Ericomp themocyler, using primers at both ends of the fragment. The primer used at the end that had been cleaved with BamHI had a protruding 5' end which resulted in the addition of SphI, HindIII and EcoRI restriction sites after the PCR reaction. The SphI site was flush against the Factor X cleavage site. The resulting PCR fragment was made blunt-ended using Klenow fragment and ligated into the SmaI site of pTZ18U in order to obtain a stable copy. Using BclI and EcoRI, the fragment was cleaved out of pTZ18U and ligated into pGEX-3X that had been cut with EcoRI and partially with BclI. The resulting plasmid, pGEX-KP, now had a SphI-HindIII-EcoRI multiple cloning site, changed from BamHI-SmaI-EcoRI in PGEX-3X.

Cloning and Expression of GST-peptide Genes

Synthetic DNAs coding for CEME (Table 1A, B), CEMA (Table I, V, W) and HNP-1 (Table 1C-H) were synthesized as overlapping oligonucleotides which were annealed and ligated into pGEX-KP where HNP-1 is the human neutrophil peptide 1 and CEME is a fusion peptide made from portions of an insect defensin ceropin A and the bee venom peptide, melittin and CEMA is a variant of CEME with two additional lysine residues at the carboxy-terminal end (FIG. 3). However, since these genes are wholly synthetic, virtually any peptide sequence or variant of CEME and HNP-1 can be incorporated (FIG. 2). Positive clones were identified by slot lysis gel electrophoresis and confirmed by DNA sequencing on an Applied Biosystems automated DNA sequencer, using synthetic oligonucleotides as primers (Table 1 T-U). Strains containing the recombinant vectors were tested for fusion protein expression. Briefly, cells were grown in Luria broth to $OD_{600}$~1.0. IPTG was added to 0.2 mM to induce expression. Samples of uninduced and induced cells were resuspended in loading buffer and subjected to SDS polyacrylamide gel electrophoresis, revealing that the fusion protein constituted as much as 15% of total cellular protein. In the case of HNP-1, the resultant fusion protein was unstable, due to proteolysis. Inclusion of a synthetic, pre-pro defensin-encoding DNA cassette rendered the fusion protein stable to proteolysis.

Purification and Cleavage of the GST-peptide Protein

Figure 5:
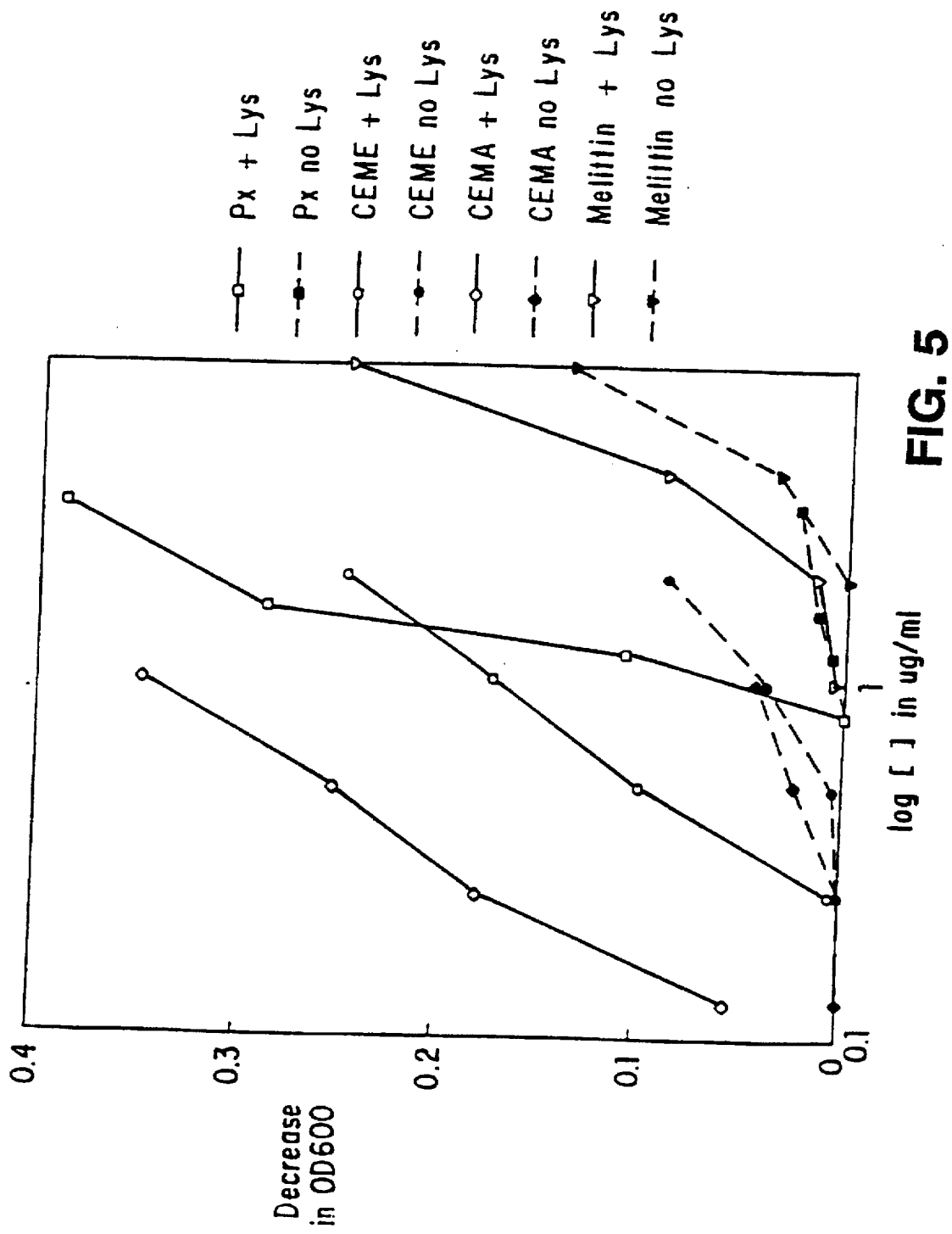
FIG. 5 shows a lysozyme lysis assay for *P. aeruginosa* treated with polymyxin B (Px), CEME, CEMA, or melittin.

Cells induced for the production of the fusion protein were harvested and lysed by passage through a French pressure cell (15000 psi). The lysate was fractionated by centrifugation at 3000×g and the fusion protein was found in either the pellet (as inclusion bodies) or in the supernatant. If found in the soluble supernatant fraction, the fusion protein was then incubated with glutathione-agarose or glutathione-sepharose beads (sulfur linkage, Sigma). The beads bound the fusion protein and were washed with several volumes of buffer to remove unbound protein. The bound fusion protein was then eluted with 0.5% SDS in order to ensure complete recovery. FIG. 5 shows the results of a typical isolation procedure. SDS removal was achieved by $CHCl_3MeOH$ (2:1) extraction or ethanol precipitation of the protein, followed by lyophilization. If found in the insoluble pellet fraction, the protein was isolated by extraction with 3% octylpolyoxyethylene (O-POE) which removes membrane proteins which are the major contaminating species in inclusion body preparation. All detectable levels of membrane proteins are solubilized with O-POE, leaving a relatively pure sample of inclusion bodies. This sample is extracted with 8M urea to solubilize the inclusion bodies, after which the urea is removed by dialysis. At this stage we attempted to release the peptide using Factor Xa protease cleavage, but found this to be extremely inefficient. Therefore, a synthetic methionine residue codon was placed immediately adjacent to the polycationic peptide sequence to permit chemical cleavage. In this case, after the inclusion body preparation was extracted with O-POE, the inclusion bodies were solubilized directly in 70% formic acid, to which CNBr was added in order to release the polycationic peptide from the fusion protein. In the final invention the methionine residue is always present.

TABLE 1

| Sequence 5' → 3' | Description |
| --- | --- |
| A) CGGGGATCCGCATATGAAATGGAAACTGTTCAAGAAGA TCGGCATCGGCGCCGTGCTGAAAGTGCTGACCACCGGT CTGCCGGCGCTGATCAGCTAACTAAGTA | 104 mer encoding CEME |
| B) AGCTTACTTAGTTAGCTGATCAGCGCCGGCAGACCGGT GGTCAGCACTTTCAGCACGGCGCCGATGCCGATCTTCTT GAACAGTTTCCATTTCATATGCGGATCCCCGCATG | 112 mer encoding CEME |
| C) GGGAGCTCCTAACTAACTAAGGAGGAGACATATGAAAC AAAGCACTATTGCACTGGCACTCTTACCGTTACTGTTTAC CCC | 81 mer used in construction of HNP-1 gene |
| D) CCAGTGCAATAGTGCTTTGTTTCATATGTCTCCTCCTTA GTTAGTTAGGAGCTCC | 56 mer used in construction of HNP-1 gene |
| E) TGTGACAAAAGCCGCATGCTACTGCCGTATACCGGCCT GCATCGCGGGCGAACGTCGTTACGGTA | 65 mer used in construction of HNP-1 gene |
| F) CAGGCCGGTATACGGCAGTAGCATGCGGCTTTTGTCAC AGGGGTAAACAGTAACGGTAAGAGTG | 64 mer used in construction of HNP-1 gene |
| G) CCTGCATCTACCAGGGCCCTCTGTGGGCGTTCTGCTG CTAAAAGCTTCGC | 50 mer used in construction of HNP-1 gene |
| H) GCGAAGCTTTTAGCAGCAGAACGCCCACAGACGGCCC TGGTAGATGCAGGTACCGTAACGACGTTCGCCCGCGATG | 76 mer used in construction of HNP-1 gene |
| I) CCATATGAGGACCCTCGCCATCCTTGCTGCCATTCTCCT GGTGGCCCTGCAGGCCCAGGCTGAGCCACTCCAGGCAA GAGCTGATGAGGTTGCAGCAGCCCCGGAGCAGA | 110 mer used in construction of pre pro cartridge |
| J) TTGCAGCTGACATCCCAGAAGTGGTTGTTTCCCTTGCAT GGGACGAAACGTTGGCTCCAAAGCATCCAGGCTCAAGG AAAAACATGGCATG | 91 mer used in construction of pre pro cartridge |
| K) CCATGTTTTTCCTTGAGCCTGGATGCTTTGGAGCCAAGC TTTCGTCCCATGCAAGGGAAACAACCACTTCTGGGATG TCAGCTGCAATCTGCTCCGGGGCTGCTGCAAC | 109 mer used in construction of pre pro cartridge |
| L) CTCATCAGCTCTTGCCTGGAGTGGCTCAGCCTGGGCCTG CAGGGCCAGCAGGAGAATGGCAGCAAGGATGGCGAGG GTCCTCATATGGCATG | 92 mer used in construction of pre pro cartridge |
| M) AGCTTGTCGACA | 12 mer encoding a HindIII to SalI adaptor |
| N) CGTCGACATCGAAGGTCGTGCATG | 24 mer encoding factor $X_a$ recognition site and an SphI to SalI adaptor |
| O) CACGACCTTCGATGTCGACGCATG | 24 mer encoding factor X recognition site and an SphI to SalI adaptor |
| P) AATTCGGATCCG | 12 mer encoding an EcoR1 to BamHI adaptor |

TABLE 1-continued

| Sequence 5' → 3' | Description |
| --- | --- |
| Q) CGGATCCATGGCATG | 15 mer encoding a methionine residue and an SphI to BamHI adaptor |
| R) CCATGGATCCGCATG | 15 mer encoding a methionine residue and an SphI to BamHI adaptor |
| S) TATGGGATCCCA | 12 mer encoding an NdeI to BamHI adaptor |
| T) CCAAAATCGGATCTGATCGAAGG | 23 mer used as sequencing primer |
| U) CAGATCGTCAGTCAGTCACG | 20 mer used as sequencing primer |
| V) GGCGCTGAAGCTAACTAAGTAAGCTTG | 27 mer encoding CEMA |
| W) AATTCAAGCTTACTTAGTTAGCTTCAGCGCC | 31 mer encoding CEMA |

EXAMPLE 2

Construction of pPA Vectors Containing CEME and HNP-1

Figure 2A:
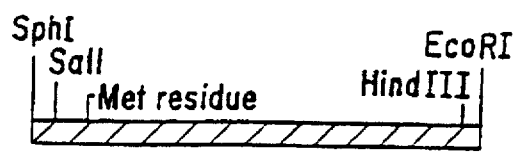
FIG. 2A–2F shows a schematic representation of constructs used in fusion protein vectors.
Figure 2B:

Using a cloned copy of the CEME gene (FIG. 2A), oligonucleotides N+0 (Table 1) were annealed and cloned into the SphI site at the 5' end of the gene (FIG. 2A). The orientation was confirmed by DNA sequencing to ensure that the SalII site was 5' to the Factor Xa recognition site. Using oligonucleotide M (Table 1), a SalI site was inserted into the 3' HindIII site. The resulting construct (FIG. 2B) had a SalI cassette that could be cloned into the SalI site of pRIT5, producing pPA-CEME (FIG. 1B). The orientation of the insert was ascertained using asymmetric restriction endonuclease sites. A cloned copy of the CEMA gene was cloned into the pPA vector as described for CEME.

Figure 2C:
Figure 2D:
Figure 2E:
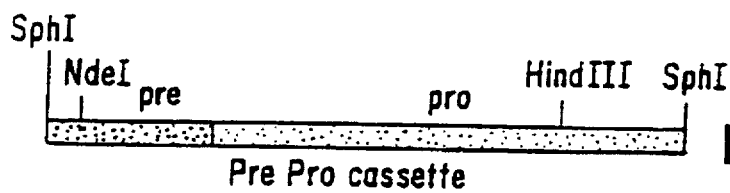
Figure 2F:
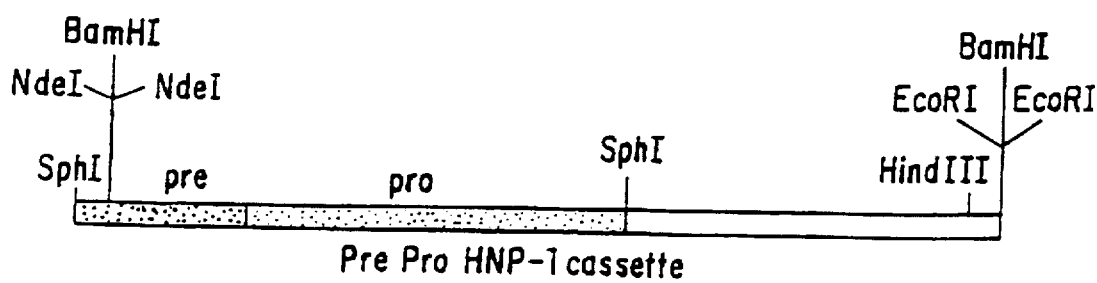

The HNP-1 gene (FIG. 2C) was altered in a similar manner using oligonucleotides Q+R (for insertion into the 5' SphI site) and oligonucleotide P (for insertion into the 3' EcoRI site). The resulting construct (FIG. 2D) had a BamHI cassette that could be cloned into the BamHI site of pRIT5 to give pPA-HNP 1. In order to examine the effects of the pre-pro cartridge in this fusion protein system, the following construct had to be made. Using the SphI sites, the pre-pro cassette (FIG. 2E) was inserted into the 5' end of the HNP-1 gene (FIG. 2C). The 3' end of this construct was changed using oligonucleotide P (Table 1) and the 5' end was altered using oligonucleotide S (Table 1). The resulting construct (FIG. 2F) was cloned into pPA-peptide using BamHI to produce pPA-proHNP1. Again, symmetric restriction endonuclease sites were used to confirm the orientation of the DNA fragment.

Production and Purification of Fusion Proteins From pPA-peptide

The plasmid pPA-CEME was transformed into *E. coli* DH5∝; however, expression attempts in this strain revealed that the heterologous protein was being proteolytically degraded. Therefore, the plasmid was transferred to *S. aureus* strain RN4220, a restriction modification mutant, (a girl from S. Kahn) using electroporation. Cells were grown in LB media supplemented with 10 µg/ml chloramphenicol to $OD_{600}$~1.0 at which time they were harvested. Culture supernatant was adjusted to pH 7.6 with NaOH and passed over an IgG Sepharose column (Pharmacia) previously equilibrated with TST (50 mM Tris-HCL pH 7.6, 150 mM NaCl+0.05% Tween 20) buffer. The column was washed sequentially with 10 volumes of TST and 5 volumes of 15 mM $NH_4Ac$ pH 5.0. Finally, the protein was eluted with 0.5M HAc pH 3.4 and directly lyophilized, to give quite a pure preparation. We have also shown that the synthetic gene for HNP-1 (with and without the pre pro cartridge) can be expressed successfully in this system with virtually no proteolytic degradation.

Cleavage of the Fusion Protein and Purification of CEME

The lyophilized heterologous protein isolated on the IgG Sepharose column was resuspended in 70% formic acid containing 1M CNBr, and the reaction was allowed to proceed for 18 hrs at 25° C. in the dark. The reaction was quenched by diluting the sample to 5% formic acid and lyophilizing it. The sample was resuspended in 0.1% trifluoroacetic acid, loaded onto a ProRPC FPLC column (Pharmacia) and eluted with a 0–40% gradient of acetonitrile+T 0.1% TFA. The CEME peptide eluted between 30–35% resulting in a partially purified sample.

Antibacterial Activity of CEME

A sample of the partially purified CEME protein was electrophoresed on a 15% acid-urea gel, which separates proteins based on charge and mass (Panyim and Chalkey, *Arch. Biochem. Biophys.*, 130:337, 1969). The pH of the buffer is acidic (≈pH 5.0) and the polarity is reversed such that proteins migrate to the cathode. Therefore, the small cationic peptides run relatively quickly through the gel and thus can be easily identified. Antibacterial activity was tested as previously described (Hultmark, *Eur. J. Biochem.*, 106:7, 1980). The gel was incubated in Mueller Hinton broth+0.2M $NaPO_4$pH 7.4 for 1 hr. It was overlaid with 5 mls of the same media containing 0.6% agar and ≈$10^5$ *E. coli* strain DC2, and then again with 5 ml of the same media containing only 0.6% agar. The overlaid gel was incubated overnight at 37° C. which resulted in zones of clearing corresponding to the migration site of melittin (positive control) and the CEME produced in this study. Melittin is used as a positive control due to its antibacterial activity and similarity in size and PI values.

Figure 4:
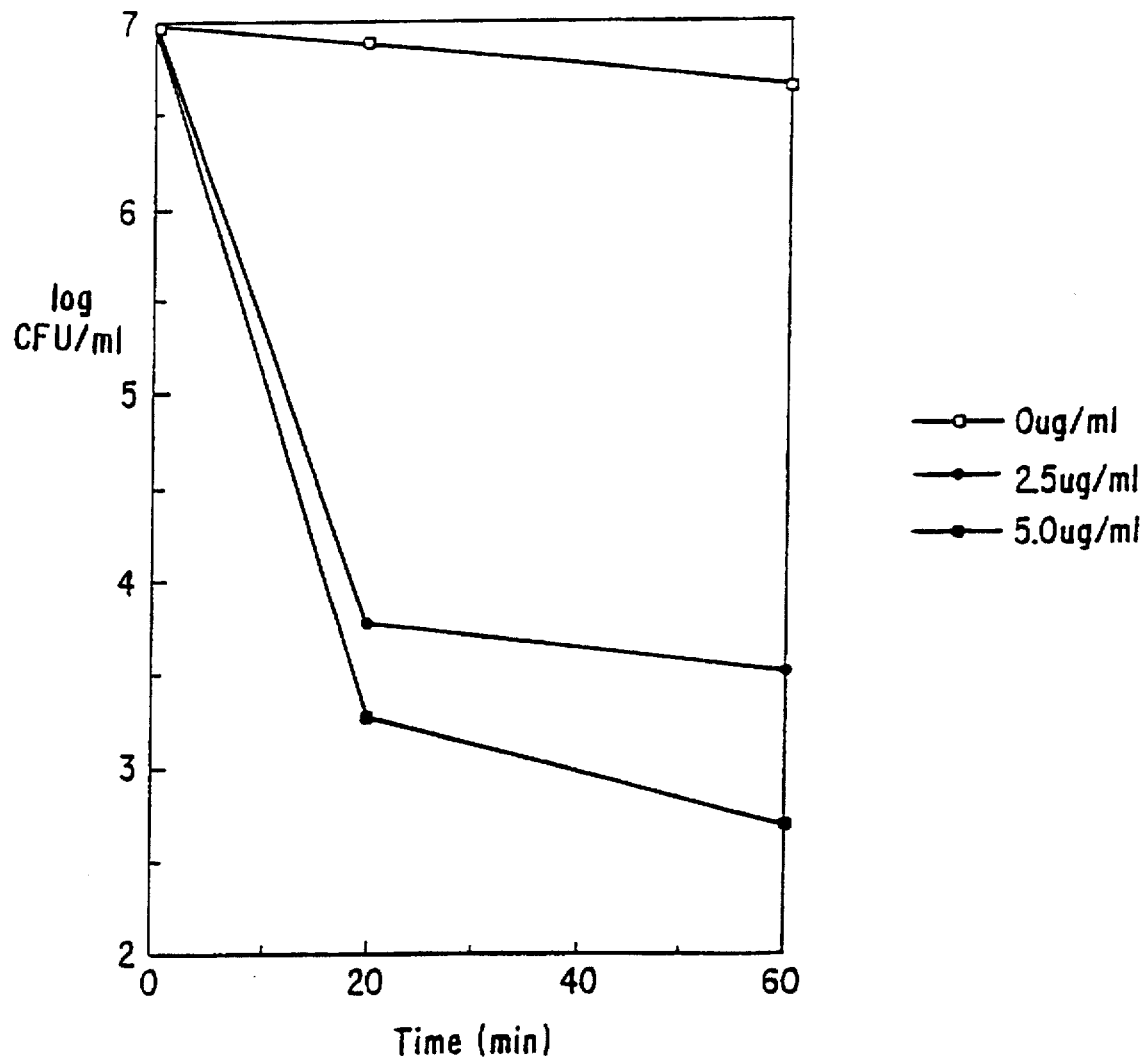
FIG. 4 shows a killing curve for *P. aeruginosa* treated with CEME.

The antimicrobial activity of CEME was also quantitated using a killing assay in which the peptide was incubated with $10^6$ cells/ml of *P. aeruginosa* for 20–60 min before the cells were plated for viability (FIG. 4). The results showed that 2.5 µg/ml (0.9 µM) of CEME reduced the viable count of *P. aeruginosa* by three log orders in 20 minutes.

The minimum inhibitory concentrations of (MIC) of CEME, CEMA and melittin were determined for a number of different bacteria (Table 2). Briefly, cells were grown overnight at 37° C. in LB-S (Luria broth without any salt supplement) and diluted one in 10,000 in the same medium to give concentrations of about $10^4$ to $10^5$ CFU/ml. The broth dilutions were set up in a 96 well microtiter plate by putting 200 µl of LB-S containing the initial concentration of antibiotic or compound in column 1 and 100 µl of the same medium in columns 2–12. The compounds were diluted by taking 100 µl of broth from column 1 and mixing it with column 2, resulting in a one in two dilution. This was continued to column 10. Finally, 10 μl of bacteria were pipetted into columns 1–11, and the plates incubated overnight at 37° C. The next day the plates were scored for growth in the wells, and the MIC determined.

Generally, CEME and CEMA had similar MIC values which were consistently lower than melittin. The MICs of the peptides were usually higher than those of polymyxin B, gentamicin (an amino glycoside) and ceftazidime (a β-lactam). Both antibiotic sensitive strains (H188 and DC2) were two- to four-fold more sensitive to the cationic peptides as compared to their parental strains. Surprisingly, the mutant SC9252 which showed an increased resistance to polymyxin B, ceftazidime, and to a lesser extent gentamicin, was not resistant to the cationic peptides. The *S. typhimurium* defensin sensitive strain (C590) was also four-fold more sensitive to CEME, CEMA and polymyxin B, and two-fold more sensitive to gentamicin and melittin. The fact that the MIC of the β-lactam ceftazidime was unchanged in this strain suggested that the mutation may be affecting the self-promoted uptake pathway, possibly by a change in the sites of initial antibiotic contact on the surface of the outer membrane. The cationic peptides were also equally active against an *E. cloacae* clinical isolate strain (218S) and its β-lactam resistant mutant (218R1, a β-lactamase overproducer). The MIC values of the peptides were slightly higher for *S. aureus* but given their much higher molecular weight they are in fact more active than most compounds on a molar basis.

with the hypothesis that the initial step in the antibacterial mechanism of cationic peptides is an association with the negatively charged sites on LPS molecules.

TABLE 3

EFFECT OF DIVALENT AND MONOVALENT CATIONS ON THE MICs OF CATIONIC PEPTIDES AGAINST *P. AERUGINOSA* H309

| Compound | MIC (ug/ml) | | |
|---|---|---|---|
|  | No addition | +5 mM Mg$^{++}$ | +80 mM Na$^+$ |
| Polymyxin | 0.5 | 1 | 0.5 |
| Gentamicin | 1 | 4 | 1 |
| Ceftazidime | 1 | 2 | 2 |
| CEME | 2.4 | 38.4 | 4.8 |
| CBMA | 2.8 | 22.4 | 5.6 |
| Melittin | 8 | >64 | 16 |

The ability of the cationic peptides to work synergistically was examined by determining the MIC values for some commonly used antibiotics in the presence of sub-MIC levels of cationic peptides (Table 4). Generally, the peptides had very little effect on the MIC of antibiotics that are proposed to be taken up through porins (ceftazidime, imipenem, and tetracycline), although CEMA at ½ MIC levels reduced their MICs 2-fold. This may be due to the high membrane permeabilizing activity of CEMA (see below). However, the peptides did lower the MIC of polymyxin B, possibly due to the fact that they are all taken up by the same pathway and are therefore aiding each other's

TABLE 2

MIC VALUES OF VARIOUS ANTIMICROBIAL AGENTS

| Bacterium | Strain | Relevant Phenotype | MIC (ug/ml)* | | | | | |
|---|---|---|---|---|---|---|---|---|
|  |  |  | PX | GM | CEF | CEME | CEMA | MEL |
| *P. aeruginosa* | H309 | Wildtype | 0.5 | 1 | 1 | 2.4 | 2.8 | 8 |
|  | H187 | Parent of H188 | 0.5 | 1 | 2 | 4.8 | 2.8 | 8 |
|  | H188 | Antibiotic sensitive | 0.06 | 0.25 | 0.03 | 1.2 | 1.4 | 8 |
| *E. coli* | UB1005 | Parent of DC2 | 0.5 | 1 | 0.5 | 2.4 | 2.8 | 8 |
|  | DC2 | Polymyxin sensitive | 0.06 | 0.5 | 0.06 | 0.6 | 0.7 | 4 |
|  | SC9251 | Parent of SC9252 | 0.06 | 2 | 0.12 | 1.2 | 1.4 | 8 |
|  | SC9252 | Polymyxin resistant | 4 | 4 | 0.5 | 1.2 | 1.4 | 8 |
| *S. typhimurium* | C587 | Parent of C590 | 1 | 4 | 0.25 | 2.4 | 5.6 | 16 |
|  | C590 | Defensin sensitive | 0.25 | 2 | 0.25 | 0.06 | 1.4 | 8 |
| *E. cloacae* | 218S | Parent of 218R1 | 0.5 | 0.5 | 0.5 | 2.4 | 2.8 | 8 |
|  | 218R1 | β-lactam resistant | 0.5 | 0.5 | >16 | 2..4 | 1.4 | 8 |
| *S. aureus* | RN4220 | Methicillin sensitive | >8 | 2 | 8 | 9.6 | >5.6 | 8 |
|  | SAP0017 | Methicillin resistant | >8 | >8 | >16 | 9.6 | >5.6 | 8 |

*PX, polymyxin B; GM, gentamicin; CEF, ceftazidime; MEL, melittin.

In addition, the MIC values for CE (the first 8 amino acid residues of CEMA) and for MA (the carboxy terminal 20 amino acids of CEMA) were all greater than 64 ug/ml in the same assay when tested on *P. aeruginosa*, *E. coli*, *S. aureus* and *Candida albicans*. Consequently, although CEMA is an effective antimicrobial agent, the individual fragments have no antimicrobial (or anti-fungal) activity.

Since divalent cations are known to stabilize the outer membranes of Gram negative bacteria by bridging adjacent lipopolysaccharide (LPS) molecules, they are able to increase the MIC values of compounds that interact with the LPS. The MIC assay was repeated in the presence of 5 mM Mg$^{++}$ and 80 mM Na$^+$ to determine whether or not this effect applied to the cationic peptides (Table 3). The results showed that the antibacterial activities of all three peptides were dramatically inhibited by the presence of Mg$^{++}$ and only minimally inhibited by Na$^+$. These data are consistent uptake. Of interest is the influence that melittin has on the MIC of polymyxin B, given the weak membrane permeabilizing activity of melittin. This may suggest that polymyxin B is disrupting the membrane, thus allowing melittin access to its target site rather than vice versa. The fact that this MIC is lower than those in the presence of CEME and CEMA may suggest that melittin is much more active at its target site than the other two peptides, and that the rate limiting step in its antibacterial activity is its transport across the outer membrane.

TABLE 4

EFFECTS OF SUB-MIC LEVELS OF CATIONIC PEPTIDES ON THE MICs OF COMMON ANTIBIOTICS

| | MIC (μg/ml) in the presence of | | | | | | |
|---|---|---|---|---|---|---|---|
| | No | CEME (μg/ml) | | CEMA (μg/ml) | | Melittin (μg/ml) | |
| Compound | peptide | 1.2 | 0.6 | 1.4 | 0.7 | 4 | 2 |
| Polymyxin | 1 | 0.25 | 0.5 | 0.12 | 0.5 | 0.06 | 0.5 |
| Ceftaxidime | 4 | 4 | 4 | 2 | 2 | 2 | 4 |
| Imipenem | 4 | 4 | 4 | 2 | 4 | 4 | 4 |
| Tetracycline | 8 | 8 | 8 | 4 | 8 | 8 | 8 |

EXAMPLE 3

Construction of pEZZ-peptide Plasmids

Figure 1D:
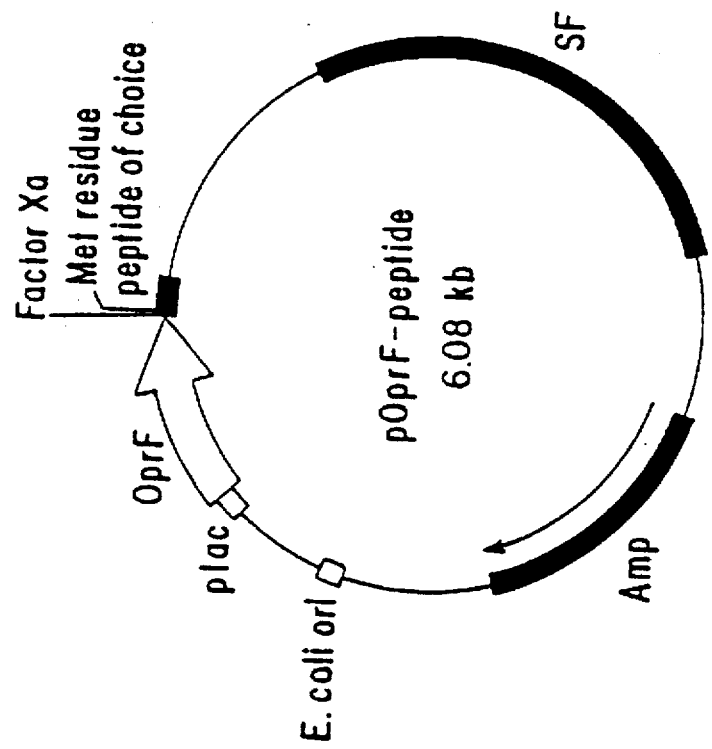
Figure 1C:
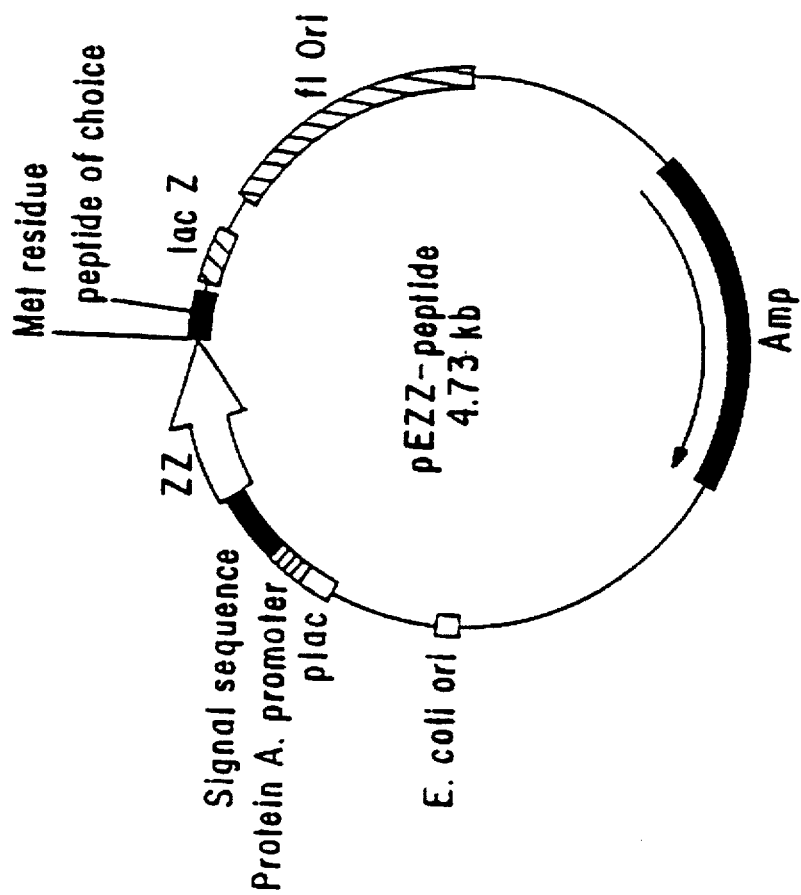

The synthetic genes for the peptides CEME and CEMA were cloned separately into the BamHI-HindIII sites of the plasmid pEZZ18 (Pharmacia) (FIG. 1C). This allowed directional insertion to occur. Clones were selected using blue/white selection by growth on IPTG-XGal media in a lac-*E. coli* strain. Correct clones were identified by restriction analysis of plasmid DNA, which was then transformed into the *E. coli* strain HB101. This strain was recommended by Pharmacia, and has been shown previously (Löwenadler, et al., *Gene*, 58:87, 1987), to allow the release of fusion protein into the external medium.

Cells harboring the clones were grown to log-phase and harvested. Whole cell lysates were electrophoresed on an SDS polyacrylamide gel, and the proteins were transferred to nitrocellulose. Using antisera specific to the peptides, the fusion proteins were identified.

Construction of pOprF-peptide Plasmid

The SalI fragment used in construction of the pPA-CEME, was utilized here. pOprF DNA (FIG. 1D) was isolated and digested with SalI to produce a linear fragment, into which the CEME cassette was ligated. Clones were analyzed at the DNA level to check for the correct orientation of the CEME DNA, using asymmetric restriction endonuclease sites. Analysis was then carded out at the protein level.

Cells were grown in selection media containing 1M IPTG. Whole cell lysates were analyzed by SDS-PAGE, and subjected to western blotting. Antisera used were (a) a polyclonal serum specific for CEME, and (b) a mAb for OprF. Results indicated both epitopes are expressed on the same molecule.

EXAMPLE 4

Membrane Permeabilizing Activity

Membrane permeabilization by polycationic compounds was measured in two different assays. The first assay measured membrane disruption by the ability of lysozyme to reach the periplasm and cause cell lysis. This assay was performed on two different organisms in order to demonstrate that it is a general phenomenon. The uptake of lysozyme into whole cells due to membrane permeabilization by various compounds was previously described in Hancock, et al., *Antimicrobial Agents and Chemo.*, 19:777, 1981. Overnight cultures of *P. aeruginosa* H309 or *E. cloacae* 218R1 grown in LB-S were diluted 1 in 50 in fresh medium and grown to an $OD_{600}=0.5–0.6$. The cells were harvested in a Silencer H-103N clinical centrifuge at 1800 g for 10 min, washed once with one volume of assay buffer (5 mM HEPES pH 7.2, 5 mM KCN), and resuspended in the same buffer to an $OD_{600}$ of 0.5. Assays consisted of 600 μl of cells with 50 μg/ml of chicken egg white lysozyme and varying concentrations of cationic compounds. Cell lysis was measured as a decrease in the $OD_{600}$ in a Perkin-Elmer dual beam spectrophotometer. Parallel experiments performed without lysozyme enabled the measurement of the lytic activity of the compounds themselves. To test whether or not permeability to lysozyme could be inhibited by divalent cations, various concentrations of $MgCl_2$ were added to the assay after the addition of lysozyme and before the addition of the test compound.

Figure 6:
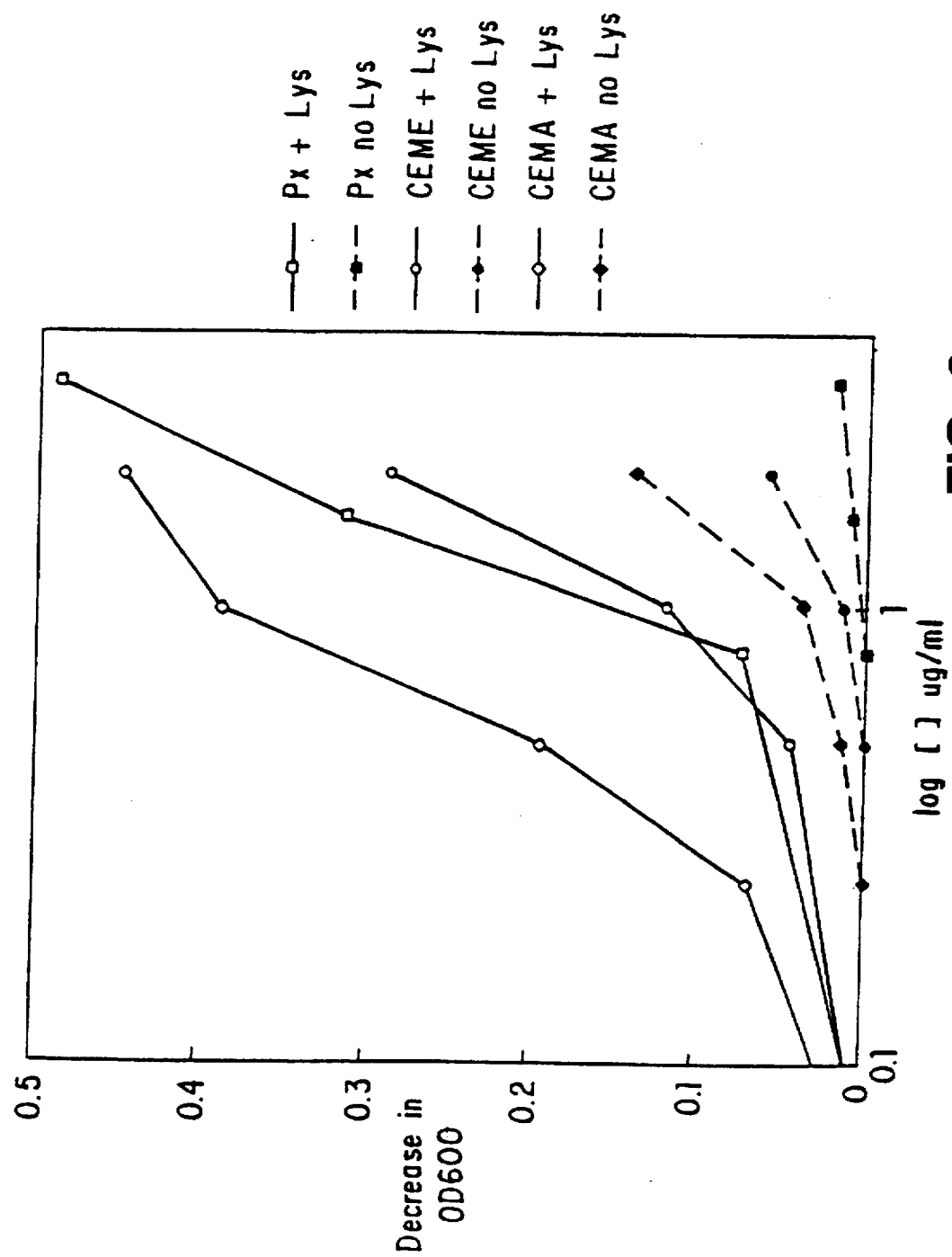
FIG. 6 shows a lysozyme lysis assay for *E. cloacae* treated with polymyxin B (Px), CEME, CEMA, or melittin.

The results show that CEMA was a stronger permeabilizer for lysozyme than polymyxin B, as was CEME, albeit only at lower concentrations (FIGS. 5 and 6). With increased concentrations of peptide, cell lysis in the absence of lysozyme occurred, especially with CEME and melittin (*P. aeruginosa* data only). When this was taken into consideration, melittin did not appear to be a good permeabilizer as compared to the other peptides, yet it is still 5- to 10- fold better than gentamicin.

Figure 7:
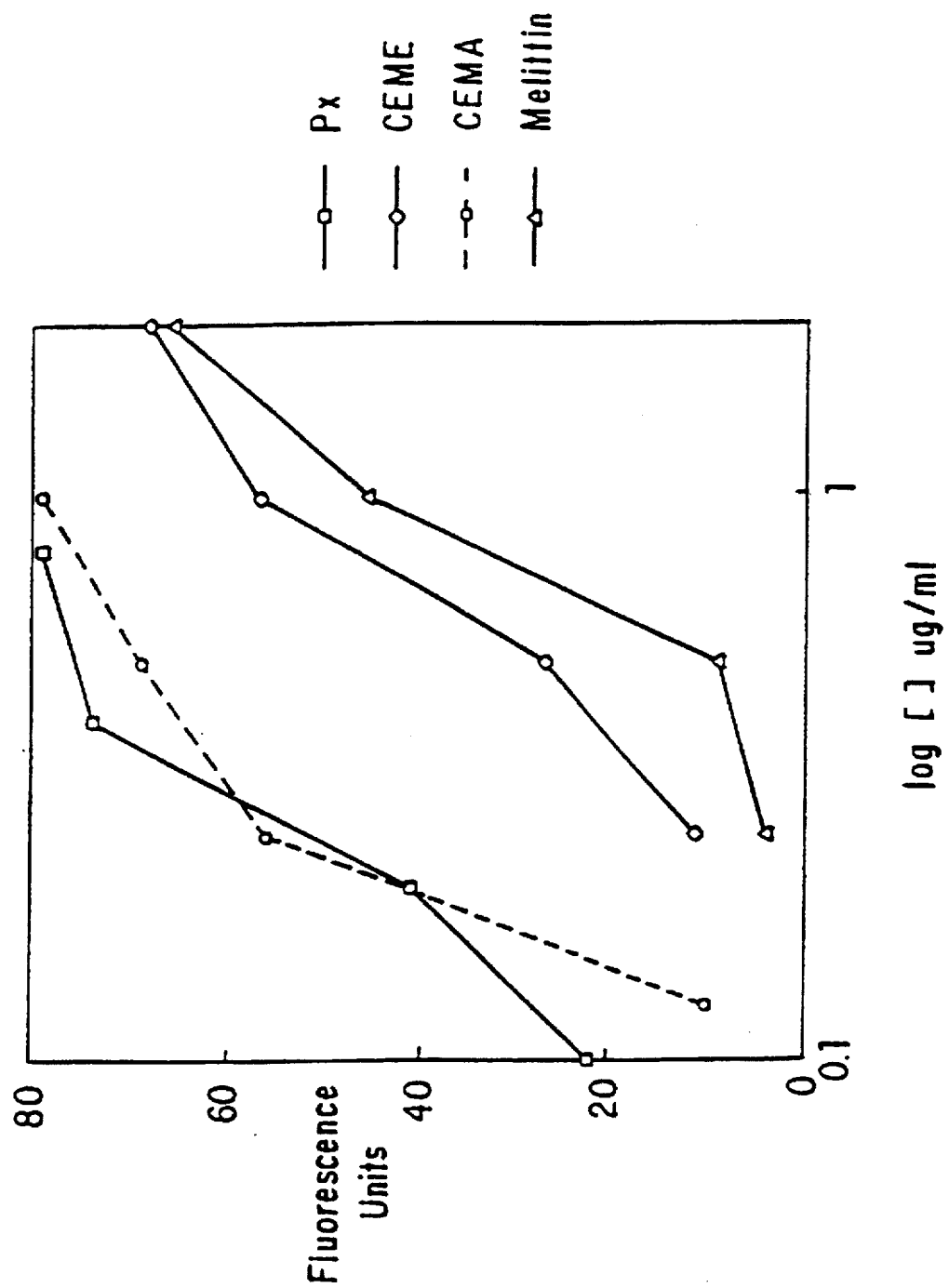
FIG. 7 shows 1-N-phenylnaphthylamine (NPN) uptake in *P. aeruginosa* after treatment with polymyxin B (Px), CEME, CEMA, or melittin.
Figure 8:
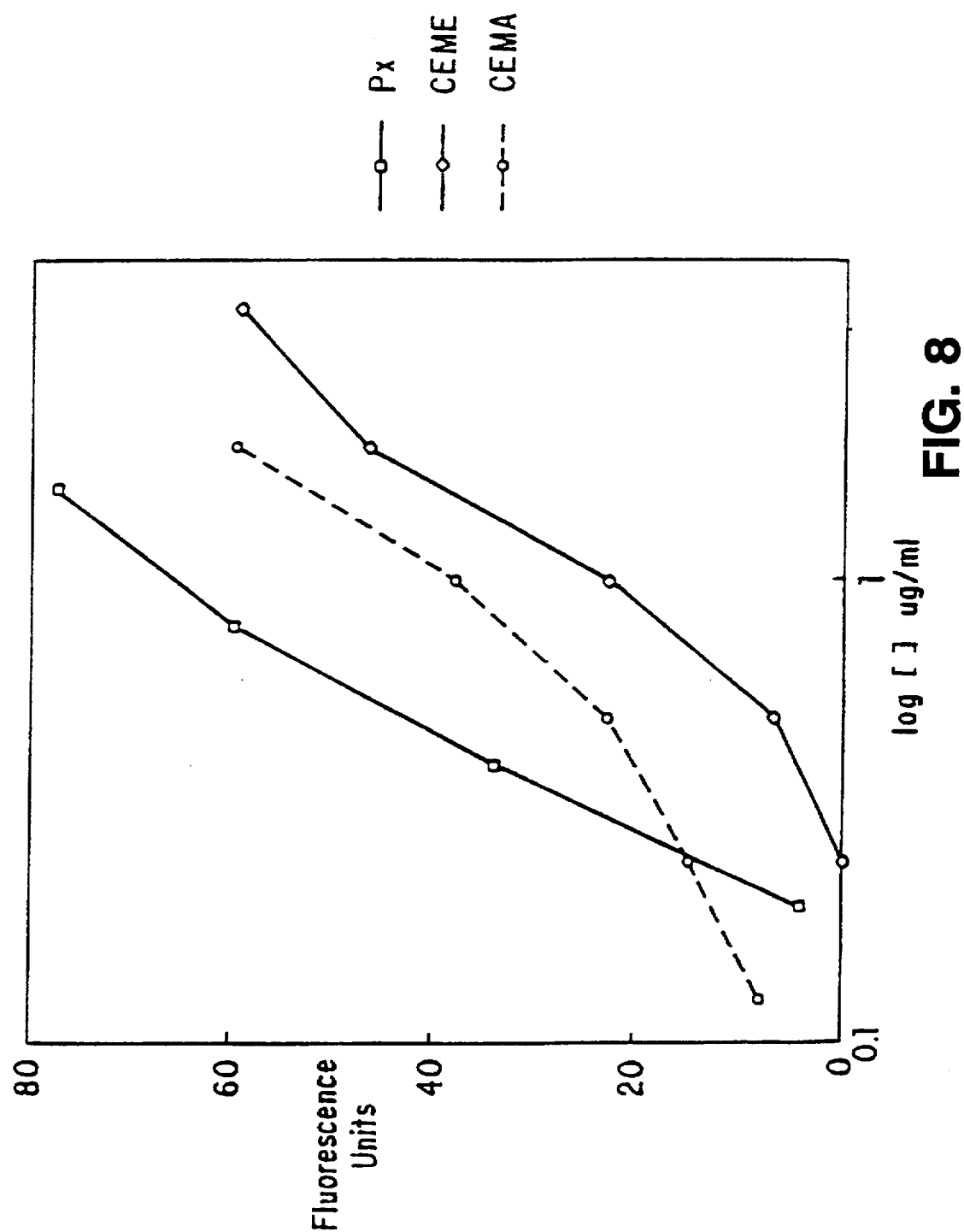
FIG. 8 shows 1-N-phenylnaphthylamine (NPN) uptake in *E. cloacae* after treatment with polymyxin B (Px), CEME, CEMA, or melittin.

The second assay determined membrane permeability by the ability of 1-N-phenylnaphthylamine(NPN), a small fluorescent probe, to insert itself into the membrane. Normally, very little NPN can penetrate the outer membrane, but in the presence of a membrane permeabilizer it can insert into the hydrophobic membrane resulting in an increase in fluorescence (FIGS. 7 and 8). This N-phenylnaphthylamine uptake assay was previously described by Loh, et al., *Antimicrobial Agents and Chemo.*, 26:546, 1984. Cells were prepared exactly the same as for the lysozyme lysis assay. 1-N-phenylnaphthylamine(NPN) was dissolved in acetone at a concentration of 500 μM. NPN fluorescence was measured in a Perkin-Elmer 650-10S fluorescent spectrophotometer using excitation and emission wavelengths set to 350 nm and 420 nm respectively, with slit widths of 5 nm. The assay was standardized by adding 20 μl of NPN (final concentration of 10 μM) and 10 μl of 0.64 mg/ml of polymyxin B (final concentration of 6.4 μg/ml) into 1 ml of cells, and adjusting the resulting fluorescence to read 90% deflection (90 arbitrary units). Various compounds were tested by adding 10 μl of different concentrations to a cuvette containing 1 ml of cells and 10 μM NPN. Permeabilizing activity was designated as the total fluorescence minus the fluorescence due to NPN alone. Following the fluorescence measurement, the $OD_{600}$ of the cells was taken to ensure no significant cell lysis had occurred. Control experiments showed that neither acetone nor test compound alone resulted in an increase in fluorescence in the absence of NPN.

In these experiments, polymyxin B and CEMA were found to be equally active in opening up the membrane to NPN, while CEME and melittin (for *P. aeruginosa*) were less active. In summary, the cationic peptides were found to be strong permeabilizers of the outer membrane, which undoubtedly contributes to their mechanism of antibacterial activity.

EXAMPLE 5

Interaction of Cationic Peptides with LPS

The MIC assays in the presence of divalent cations indicated that the cationic peptides associated with the negatively charged sites on the LPS. To further demonstrate this quantitatively, dansyl polymyxin (DPx) displacement assays were performed using purified *P. aeruginosa* LPS.

Figure 9:
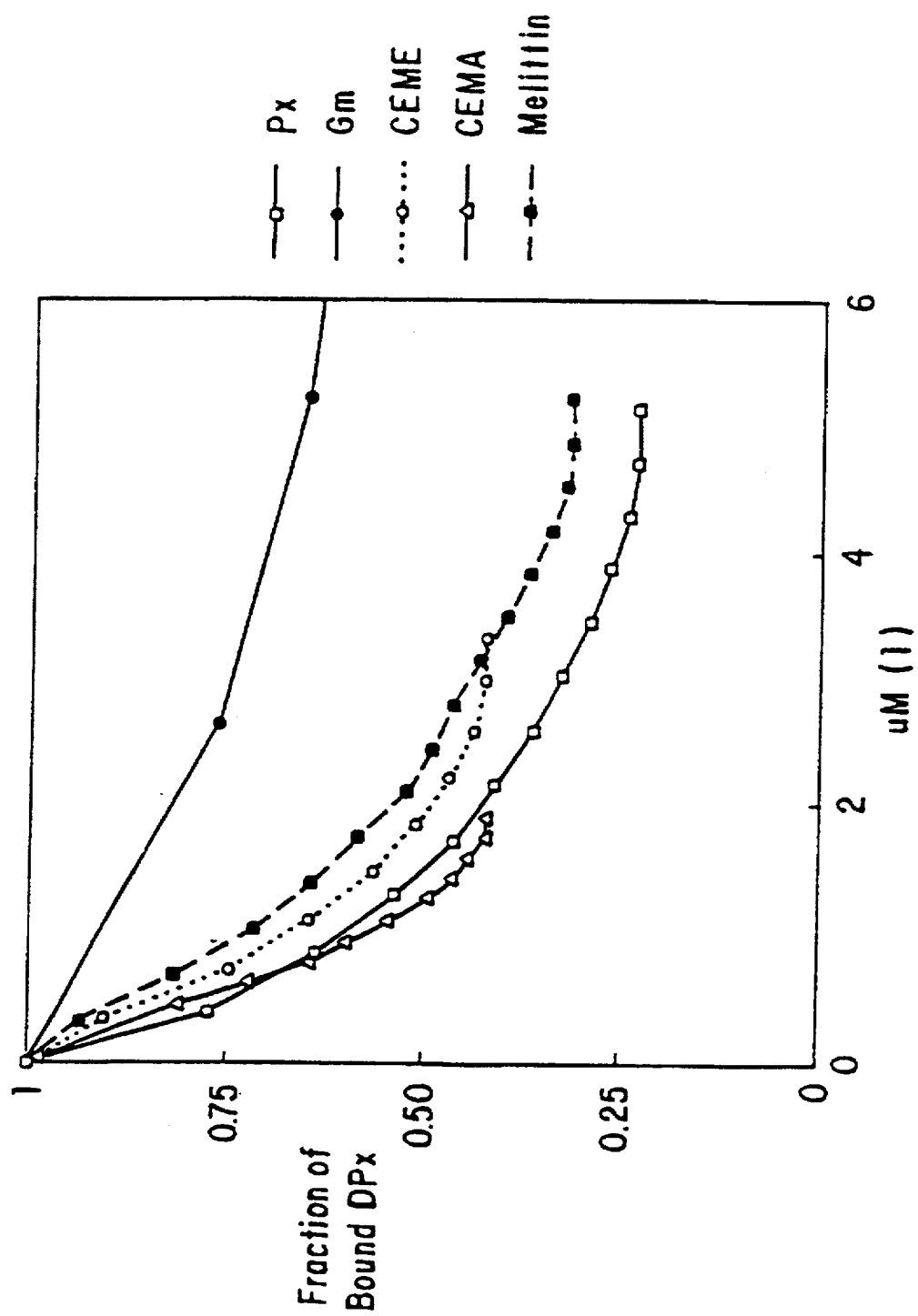
FIG. 9 shows inhibition of dansyl polymyxin (DPx) binding to *P. aeruginosa* lipopolysaccharide (LPS) by polymyxin B (Px), gentamicin (Gm), CEME, CEMA, or melittin.

DPx is a derivative of polymyxin that fluoresces strongly when bound to LPS, but weakly when free in solution. In this assay, DPx was incubated with LPS to saturate the binding sites and then, while polycationic compounds are titrated into the reaction, displacement of the DPx was monitored by the decrease in fluorescence (FIG. 9). *P. aeruginosa* LPS was isolated as previously described (Darveau, et al., *J of Bacteriology*, 155:831, 1983) Dansyl polymyxin was synthesized as described by Schindler, et al., *B. Antimicrobial Agents and Chemo*, 8:95, 1975.

Briefly, 40 mgs of polymyxin B and 10 mgs of dansyl chloride were mixed in 2 mls of 60 mM $NaHCO_3$ and 40% acetone and incubated in the dark for 90 minutes. The unreacted dansyl chloride was separated from the dansyl polymyxin by gel filtration on a Sephadex G-50 column. The fractions containing dansyl polymyxin were extracted with ½ volume of n-butanol and then evaporated to dryness in a desiccator at 37° C. The dansyl polymyxin was resuspended in 5 mM Hepes pH 7.0, quantitated by dinitrophenylation and stored in aliquots at −20° C.

The method of Moore, et al., (*Antimicrobial Agents and Chemo.*, 29:496, 1987), was used to test how much DPx was needed to saturate the binding sties on LPS. Briefly, 5 μl samples of 100 μM DPx were titrated sequentially into 1 ml of 3 μg/ml of LPS until a maximum fluorescence was reached. The fluorescence was measured in a Perkin-Elmer 650-10S fluorescence spectrophotometer with an excitation wavelength of 340 nm and an emission wavelength of 485 nm using slit widths of 5 nm. Final concentration of DPx giving 90–100% maximum fluorescence (2.5 μM) was chosen and used in all subsequent experiments. For the binding inhibition assays (Moore, et al., *Antimicrobial Agents and Chemo.*, 29:496, 1987), 2.5 μM DPx was added to 3 μg/ml of H103 LPS in 5 mM HEPES pH 7.2. The test compounds were added 5 μl at a time and the decrease in fluorescence due to displacement of the DPx from the LPS was recorded. The addition of the compound was continued until it resulted in only a small ((5%) decrease in fluorescence. The data was plotted as 1-{(maximum fluorescence-test fluorescence)/ maximum fluorescence} versus the compound concentration (I). To determine the relative affinities of the compounds for the binding sites on LPS, a double reciprocal plot was made, plotting 1/(maximum fluorescence-test fluorescence)/ maximum fluorescence versus 1/I. The calculated x-intercept was equivalent to $-1/I_{50}$, where $I_{50}$ equals the concentration of the compound which displaces 50% of the DPx bound to LPS. All experiments were performed a minimum of three times.

For DPx binding inhibition assays using whole cells instead of purified LPS, H309 cells were prepared the same way as for the lysozyme lysis assay. The assay consisted of 10 μl of cells at an $OD_{600}$ of 0.5, 990 μl of 5 mM HEPES pH 7.2 and 5 mM KCN, and the concentration of DPx that gave 90–100% binding saturation. This concentration varied from day to day but usually was between 2.5 μM and 3.5 μM. Compounds were titrated in, and $I_{50}$ values were determined as described above.

Figure 10:
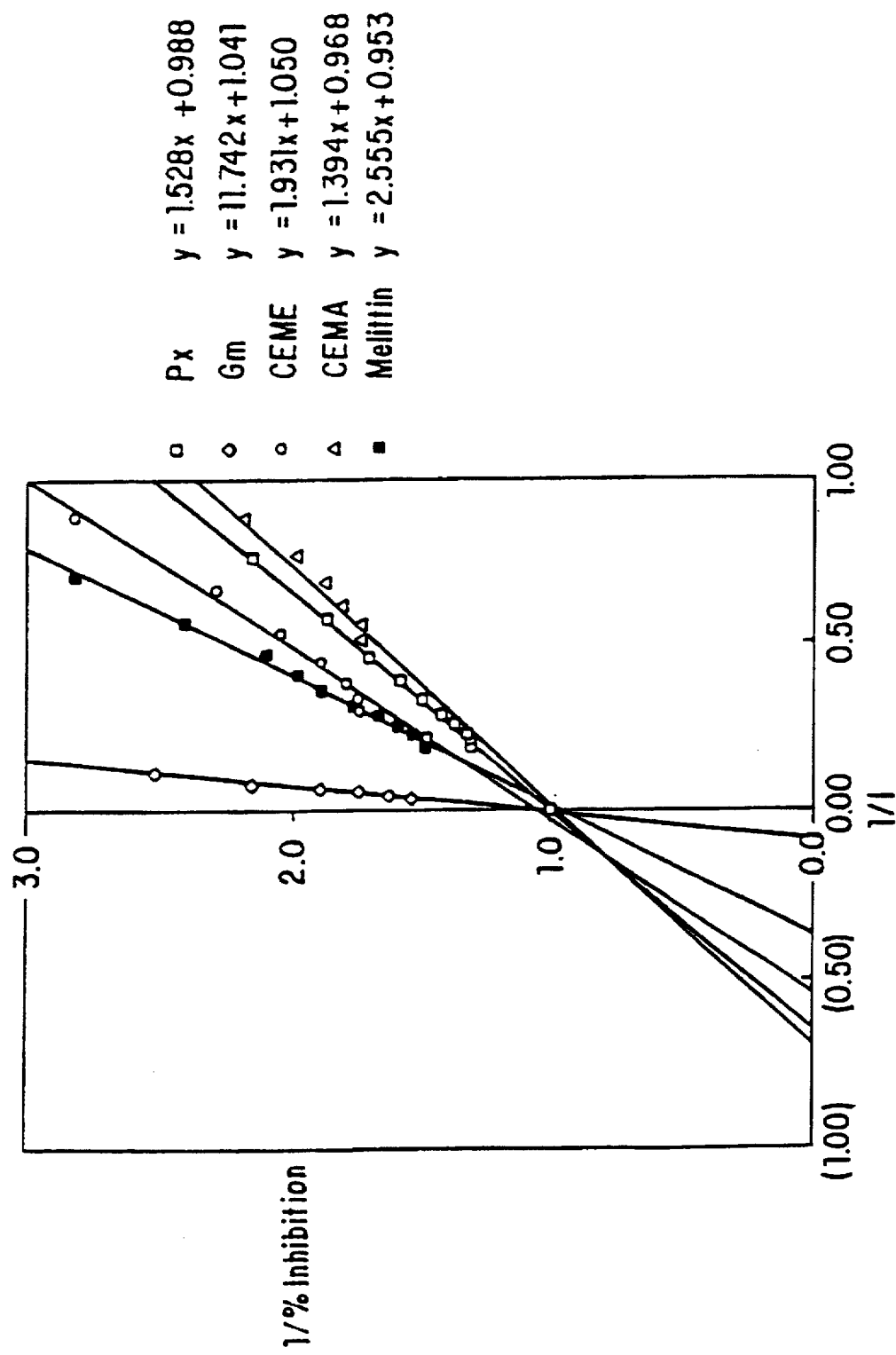
FIG. 10 is a double reciprocal plot of the results shown in FIG. 9.

The data showed that the cationic peptides displaced DPx at concentrations comparable to that of polymyxin B but much higher than that of gentamicin, thus indicating a strong affinity for the LPS. When the data was plotted as a double reciprocal plot (FIG. 10), the X-intercept provided a value that is equal to $-1/I_{50}$. $I_{50}$ is a measure of the affinity of a compound for LPS and is equal to the concentration of compound at which 50% maximal DPx displacement occurred (Table 5). The data indicated that CEMA had a higher affinity for LPS than polymyxin B (on a μM basis) with CEME and melittin having slightly lower affinities.

TABLE 5

$I_{50}$ VALUES FOR VARIOUS COMPOUNDS AGAINST *P. aeruginosa* LPS AND WHOLE CELLS[a]

| Compound | *P. aeruginosa* H103 LPS | | *P. aeruginosa* H309 Whole Cells | |
|---|---|---|---|---|
| | Value in μM | Value in μg/ml | Value in μM | Value in μg/ml |
| Polymyxin | 1.51 ± 0.04 | 2.97 ± 0.07 | 2.04 ± 0.65 | 3.7 ± 1.20 |
| Gentamicin | 19.25 ± 7.18 | 18.16 ± 6.77 | 39.13 ± 9.67 | 36.92 ± 9.12 |
| $MgCl_2$—$6H_2O$ | 1293 ± 270 | 262 ± 54.8 | 203 ± 101.00 | 41.2 ± 20.50 |
| CEME | 3.52 ± 1.45 | 9.51 ± 3.91 | 0.78 ± 0.04 | 2.11 ± 0.11 |
| CEMA | 1.32 ± 0.117 | 4.12 ± 0.36 | 0.37 ± 0.03 | 1.15 ± 0.09 |
| Melittin | 2.97 ± 0.506 | 8.48 ± 1.44 | 0.48 ± 0.08 | 1.37 ± 0.22 |

[a]Values are an average of at least three trials.

Figure 11:
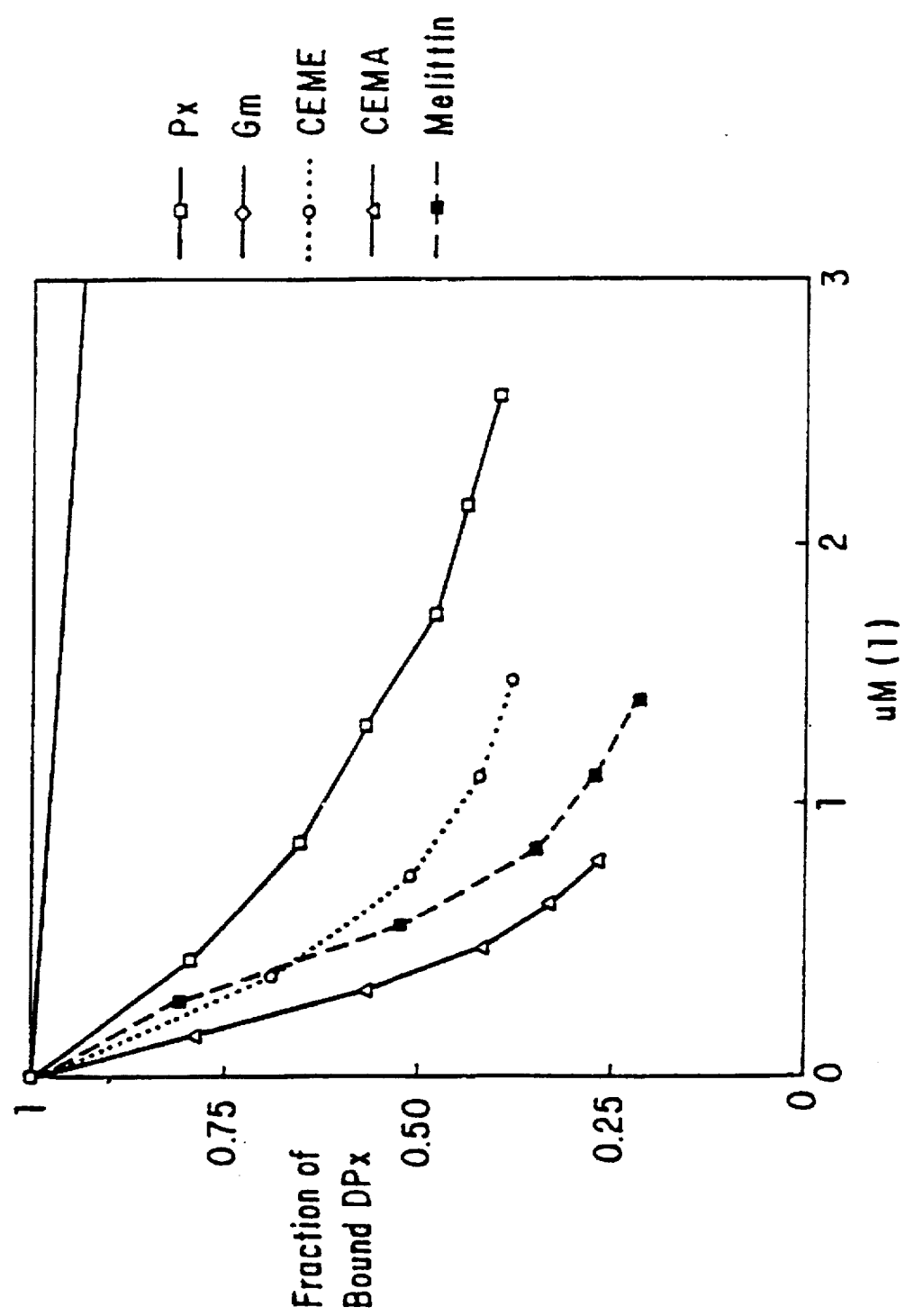
FIG. 11 shows inhibition of DPx to intact *P. aeruginosa* cells in the presence of Px, Gm, CEME, CEMA, or melittin.
Figure 12:
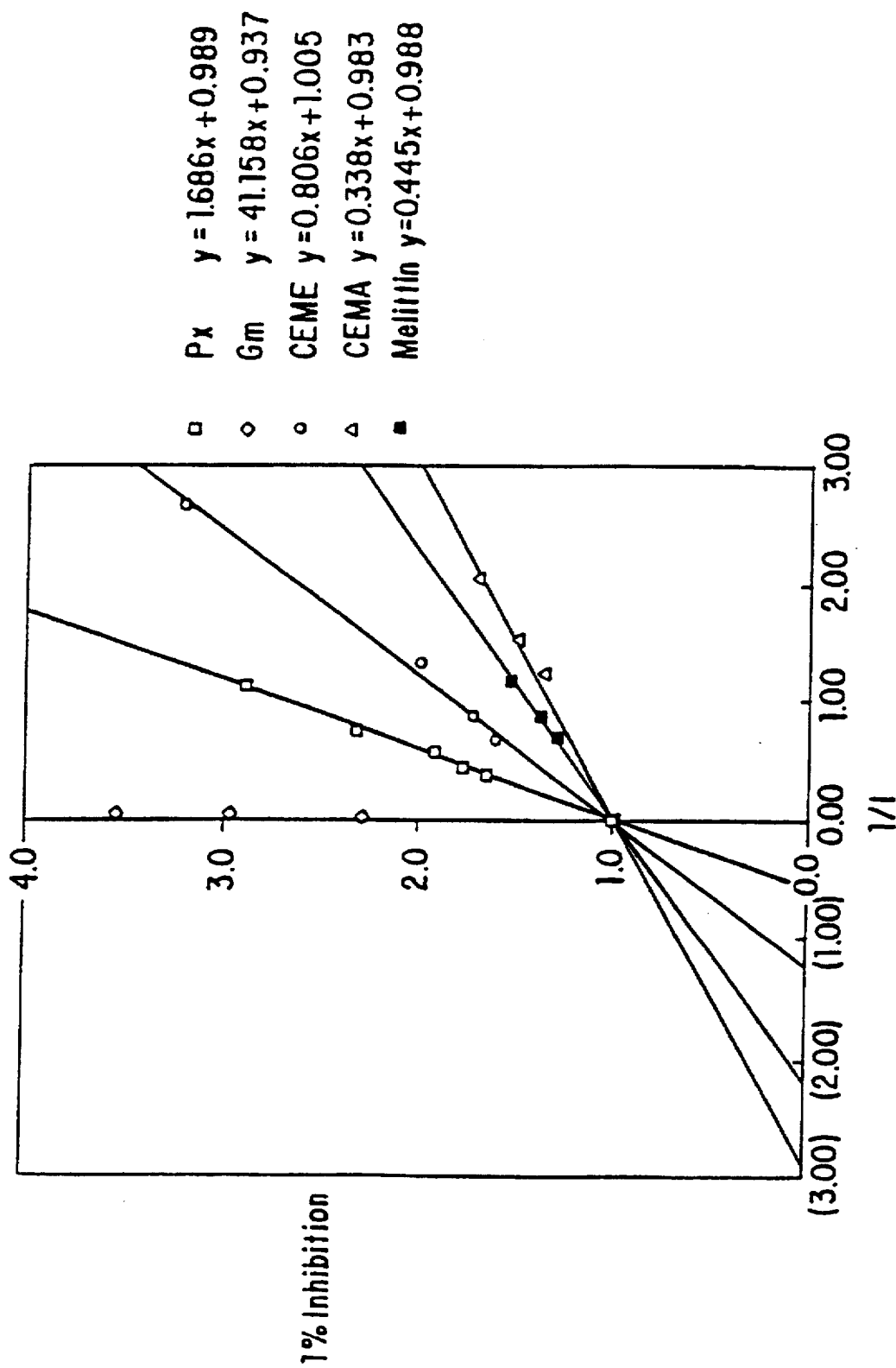
FIG. 12 is a double reciprocal plot of the results shown in FIG. 11.

To determine whether or not these affinities are biologically relevant, the experiments were repeated with intact *P. aeruginosa* cells (FIGS. 11 and 12). The $Is_{50}$ values from these experiments (Table 5) showed that all three cationic peptides were better at displacing DPx from whole cells than polymyxin B. This is interesting given that only CEMA (and CEME at low concentrations) was shown to be a better membrane permeabilizer than polymyxin B. The difference between these LPS binding affinities and subsequent membrane permeabilizing activities may be indicative of the level of competing divalent cations or the conformation that the peptides adopt once they interact with the LPS.

EXAMPLE 6

Inhibition of LPS-Mediated TNF Induction in macrophages by Cationic Peptides

The effect of CEME and CEMA peptides on LPS-induced TNF in macrophages was examined. RAW 264.7 macrophage cells were grown by seeding $10^6$ cells into a 162 $cm^2$ cell culture flask and incubated at 37° C., 5% $CO_2$ for 1 week. RAW cell media (Dulbecco's Modified Eagle Medium with Hepes buffer 450 ml; 2.4 mM L-glutamine 3 ml (400 mM); Pen/Strep 3 ml ($10^4$ U/ml of Pen, 1 mg/ml strep); and 10% heat inactivated fetal bovine serum (FBS) 50 ml) was then completely removed from flasks. 10 mls of cell dissociation solution (Sigma) was added to each flask and incubated at 37° C. for 10 minutes. Cells were removed from flasks, diluted in RAW cell media and centrifuged for 6 minutes. The cell pellet was resuspended in 5 ml of media/flask used. 1001 μl cell suspension was removed and added to 400 μl of trypan blue and cells were counted using a hemocytometer.

The cell suspension was diluted to 1×10⁶ cells/ml and 1 ml of suspension was added per well of a 24 well plate. The 24 well plates were incubated at 37° C., 5% $CO_2$ overnight for use in the assay.

After an overnight incubation, the media was aspirated from all the wells. 100 µl of Lipopolysaccharide (LPS) was added at 100 ng/100 µl. CEME or CEMA was added at the desired concentration/100 µl to specified wells. RAW cell media was added to all the wells so they all had a final volume of 1 ml. The plates were then incubated for six hours at 37° C., 5% $CO_2$. The supernatant was then removed from the wells and stored overnight at 4° C. For those wells in which whole bacteria were added directly to the wells, the supernatant was centrifuged in 0.2 µm filter eppendorf tubes for 5 minutes.

The supernatants were then used in cell cytotoxic L929 assay. The samples were transferred to 96 well plates. 50 µl of TNF media was added to all the wells in all the plates except to those wells in the first row. 10 µl of murine TNF standard (20 ng/ml) and 90 µl of TNF media was added in duplicate to the plate and diluted 1:2 down the plate to the second to last row. Test samples (75 µl), comprising of the supernatants from the RAW cell assays, were added to separate rows in duplicate and diluted 1:3 to the second to last rows.

TNF-sensitive L929 mouse fibroblast cells were grown by seeding 10⁶ cells into a 162 cm² cell culture flask and left to grow for 1 week. L929 cells were removed from the flask with 10 mls of trypsin-EDTA/flask and incubated 3–5 minutes. Cell suspension was diluted and centrifuged for 6 minutes. The pellet was resuspended in 5 mls of fresh L929 media/flask and counted (same as RAW cells). Cell suspension was diluted to 10⁶ cells/ml. 100 µl was used to inoculate each well of the 96 well plates with the supernatants. (L929 Growth Media was the same as RAW cell media except instead of FBS, 50 mls of 10% heat inactivated horse serum was utilized; TNF Assay Media was the same as RAW cell media except 4 µg/ml Actinomycin D was added.)

The plates were incubated at 37° C. at 5% $CO_2$ for 2 days. The media was then aspirated and replaced with 100 µl of the dye MTT (0.5 mg/ml) in modified Eagle Medium without phenol red. The plates were then incubated at 37° C. at 5% $CO_2$ for 3 hours. The dye was then removed and replaced with 100 µl of absolute ethanol. The plates were left at room temperature for 10–15 minutes to dissolve the formazan dye crystals.

The plates were read at 570 nm in a ELISA plate reader with 690 nm reference filter. One unit of TNF activity is defined as the amount required to kill 50% of the L929 cells. The TNF level in Units per ml therefore was the reciprocal of the dilution which led to a 50% killing of L929 cells.

Figure 13:
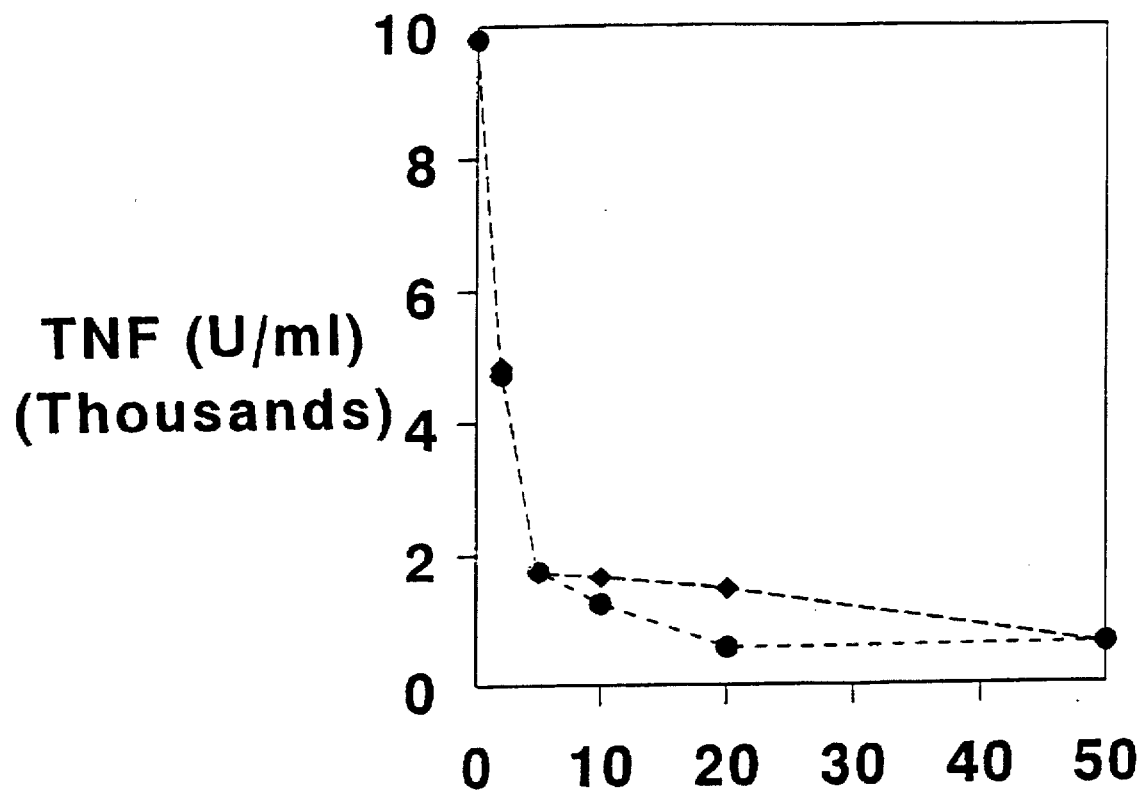
FIG. 13 shows tumor necrosis factor (TNF) levels measured 6 hours after the addition of *E. coli* 0111:B4 LPS and CEME (ME) and CEMA (MA) to macrophage cells. The data is from two separate assays.
Figure 14:
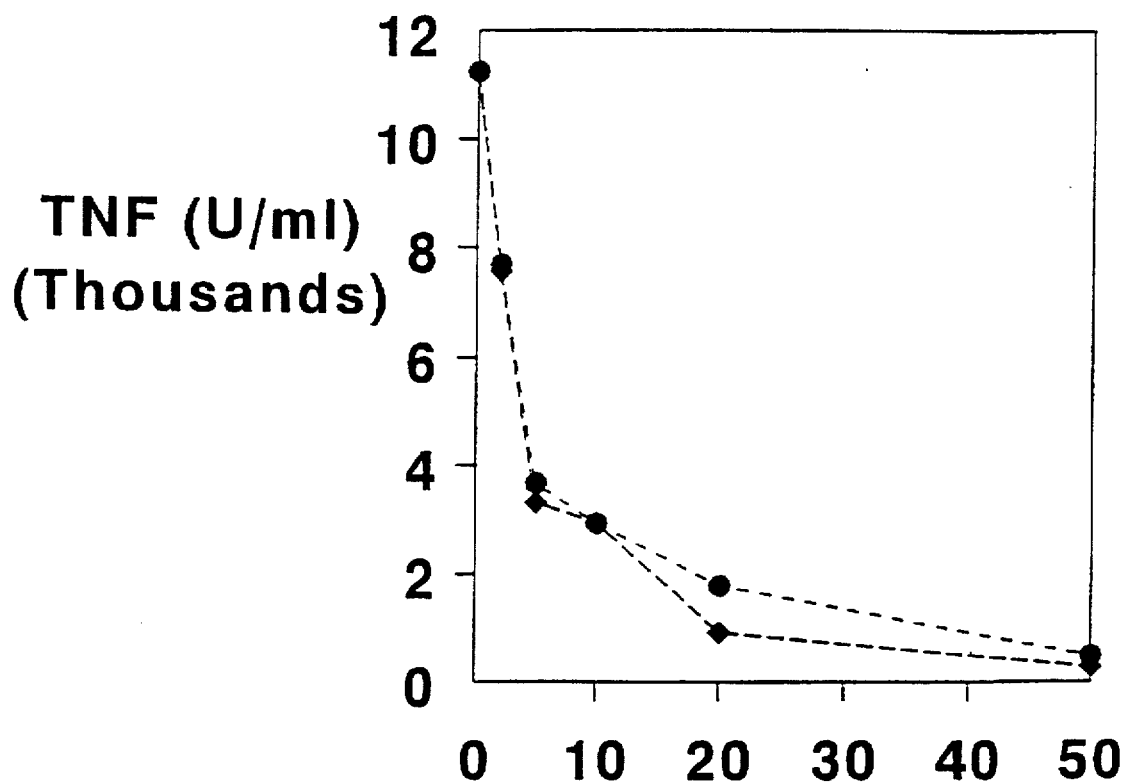
FIG. 14 shows tumor necrosis factor (TNF) levels measured 6 hours after the addition of *E. coli* Bort LPS and CEME (ME) and CEMA (MA) to macrophage cells. The data is from two separate assays.

FIGS. 13 and 14 show levels of TNF (U/ml) after a 6 hour treatment with increasing amounts (0, 2, 5, 10, 20, or 50 µg) of either CEME (ME) or CEMA (MA) peptide and 100 ng of LPS. TNF levels were measured six hours after the addition of *E. coli* 0111:B4 or *E. coli* Bort LPS (FIG. 13 and 14 respectively). The data shows the results of 2 separate experiments and indicate that both peptides efficiently reduce the level of LPS-induced TNF in the culture with two distinct LPS samples at concentrations of peptides as low as 5 µg/ml.

In intact cell induction experiments, 10⁶ *E. coli* Bort cells induced 11,967–14,805 Units of TNF per ml in RAW cells. Addition of 20 µg of CEMA resulted in a 96% or 97% reduction in TNF levels induced by 10⁶ *E. coli* Bort cells in two independent experiments.

The RAW 264.7 macrophage cell line was grown in tissue culture to 10⁶ cell per ml at 37° C. in a 5% $CO_2$ incubator. Lipopolysaccharide (LPS) from *P. aeruginosa* strain H 103 or *E. coli* were added at concentrations between 0 and 100 µg/ml with or without 1.2–2.4 µg/ml of CEME, and the cells further incubated for 6 hours at 37° C. in a 5% $CO_2$ incubator. Supernatants were then collected and assayed for TNF activity on the TNF-sensitive L929 mouse fibroblast cell line. TNF activity was defined as the reciprocal of the dilution required to produce 50% cytotoxicity relative to control cells (Table 6).

TABLE 6

INHIBITION OF TNF INDUCTION BY CEME

| Concentration of CEME (µg/ml) | Concentration of LPS (ng/ml) | TNF Induction (% of Control)* | |
|---|---|---|---|
| | | *P. aeruginosa* LPS | *E. coli* LPS |
| 0 | 10 | 100 | 100 |
| | 100 | 100 | 100 |
| 1.2 | 10 | 40 | ND |
| | 100 | 92 | ND |
| 2.4 | 10 | 10 | 9 |
| | 100 | 59 | 34 |

*Results are the averages of 3 experiments; ND = not determined.

These data in Table 6 demonstrate that CEME at the MIC (1.2–2.4 µg/ml) inhibited TNF production by LPS from more than one species of bacteria, in a dose-dependent fashion by as much as 91%.

Figure 15:
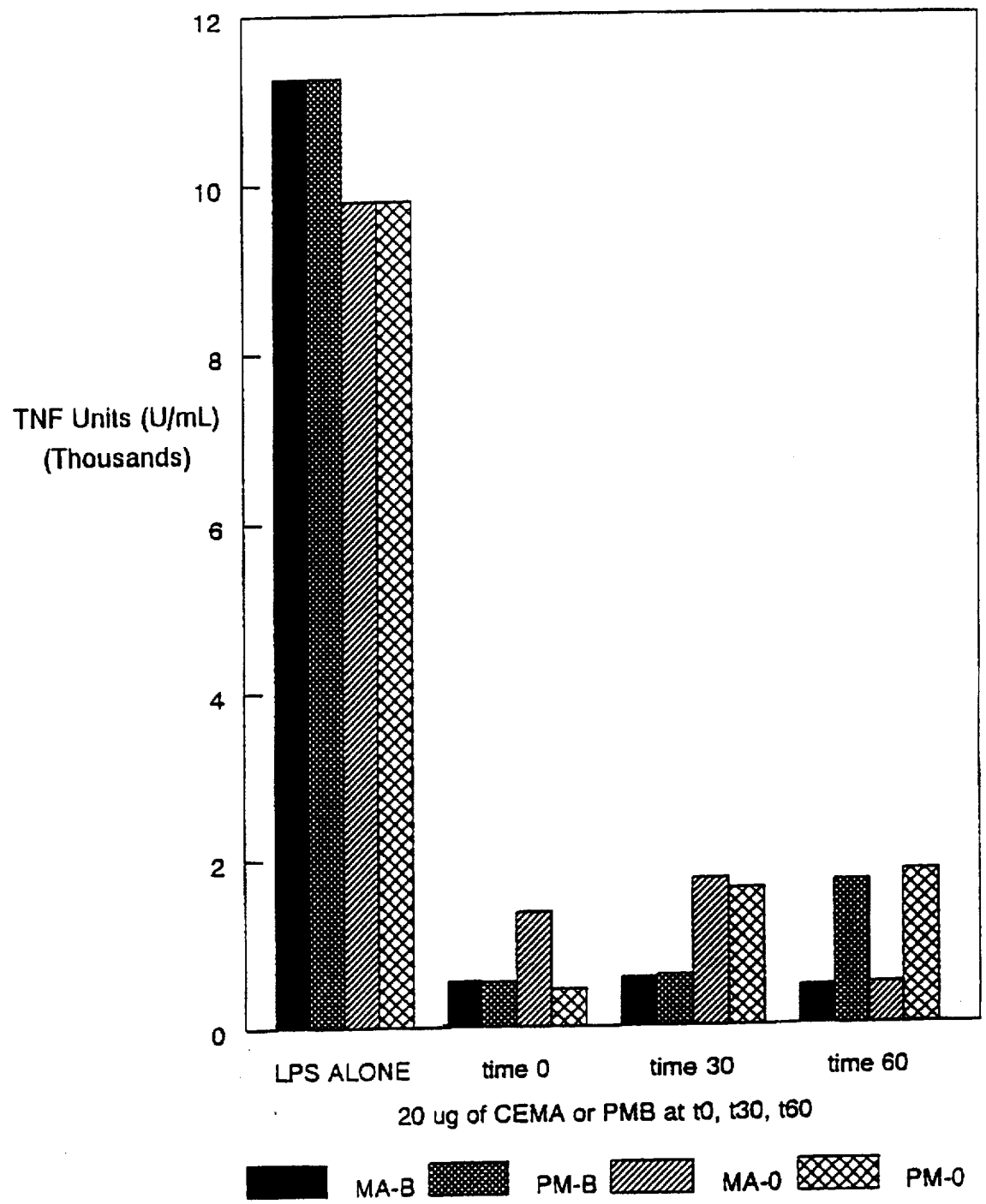
FIG. 15 shows RAW cell TNF production after addition of *E. coli* Bort and *E. coli* 0111 :B4 LPS and the effect of the addition of CEMA (MA) and polymyxin B on TNF.

In order to determine how rapidly CEMA reduced LPS-induced TNF production, *E. coli* 0111:B4 or Bort LPS was added at time 0 to RAW macrophages. CEMA or Polymyxin B was added at time 0, 30 and 60 minutes. Levels of TNF were measured after 6 hours. The results are shown in FIG. 15. (MA-B, CEMA antagonizing the effects of Bort LPS, PM-B, Polymyxin B with Bort LPS; MA-O, CEMA with 0111:B4 LPS, PM-O, Polymyxin B with 0111:B4 LPS.) The results show that CEMA inhibited TNF induction by LPS in a similar manner to polymyxin B. Furthermore, CEMA was effective at reducing the ability of LPS to induce TNF in RAW cell lines even when added 60 minutes after the addition of LPS. CEMA demonstrated a distinct and reproducible advantage over polymyxin B when added 60 minutes after the addition of LPS. To confirm that CEMA was acting on LPS rather than directly upon macrophage cell lines, 20 µg of CEMA was added to RAW cells and incubated for 60 minutes prior to aspiration of the medium and washing the cells 3 times with HBSS (Hanks Buffered Salt Solution). Addition of 10 ng or 100 ng of LPS to the washed RAW cells resulted in a high level of TNF induction (14,000–20,000 Units of TNF per ml), suggesting that the CEMA had not permanently depressed the ability of RAW cells to induce TNF in response to LPS addition. In contrast, the aspirated medium containing CEMA could depress the ability of fresh RAW cells to induce TNF in response to 10 ng or 100 ng of *E. coli* Bort LPS by 98.5% and 75% respectively. Up to 50 µg of CEMA caused no apparent decrease in RAW cell viability as judged by Trypan blue exclusion.

EXAMPLE 7

Protection from Lethal LPS Endotoxicity in a Mouse Endotoxic Shock Model

The ability of CEME and CEMA to protect against LPS-induced endotoxemia was assessed in vivo. Mice (8–10 weeks old) were injected intraperitoneally with 20 µg D-galactosamine (Dgal) to sensitize them to LPS according to the mode of Galanos (Galanos, et al., *Proc. Natl. Acad. Sci., USA*, 76:5939–5943, 1979), followed by 0, 50, 100, or 200 µg CEME or CEMA in 100 µl. Immediately afterwards LPS (10 or 20 µg) in 100 µl was injected. The mice were observed at 24 and 48 hours after injections and survivors noted.

Figure 16:
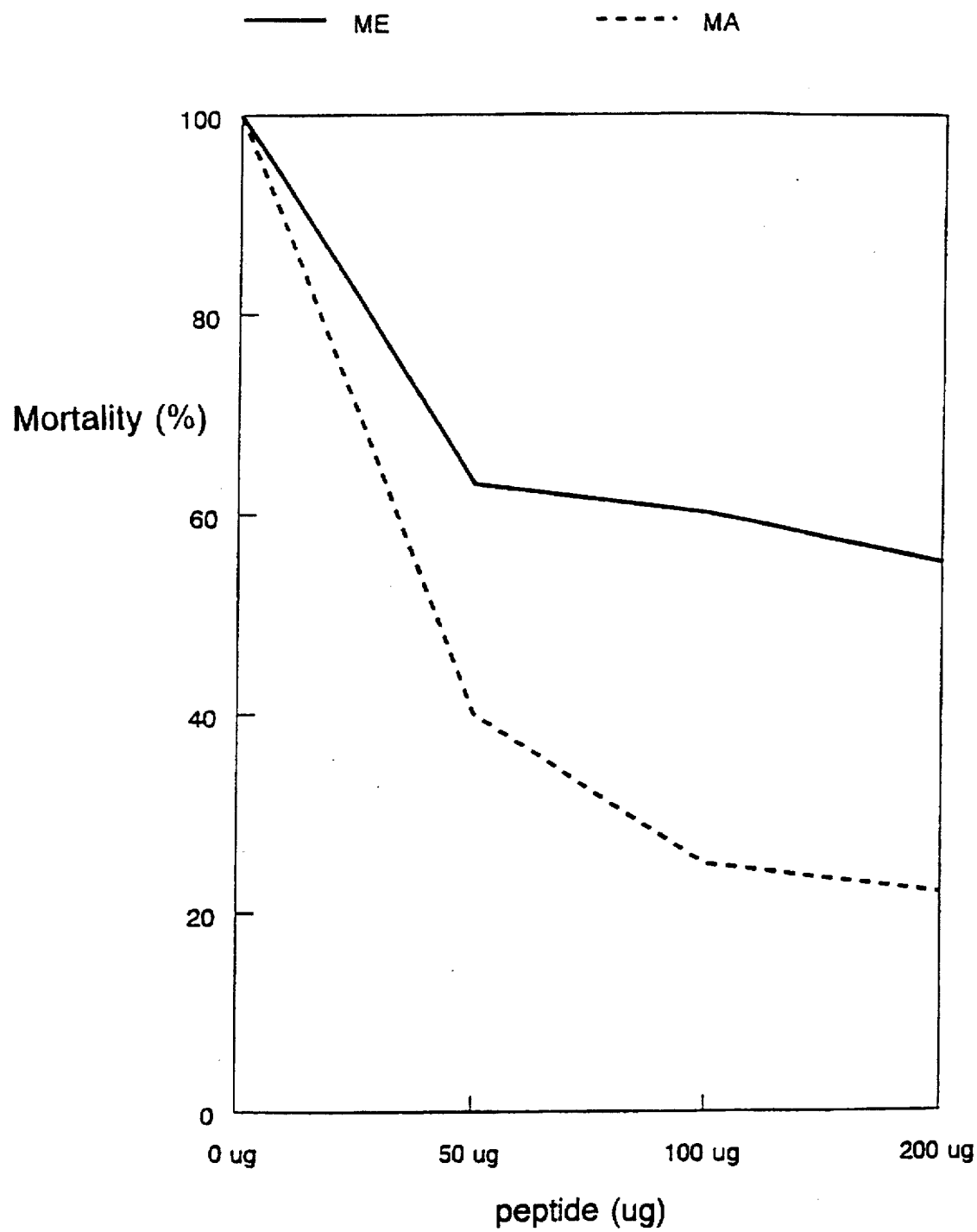
FIG. 16 shows percent mortality in mice in an endotoxic shock model after treatment with CEME or CEMA peptide at 0, 50, 100, 200 μg (2.2, 4.3 and 8.7 mg/kg respectively).

All mice given 200 µg of CEME or CEMA alone (i.e., 8.7 mg/kg) survived suggesting that such a dose was not toxic to the animals. CEME had a small protective effect (29%) when mice were challenged with a high dose (20 µg) of endotoxin (FIG. 16). In contrast, when LPS and CEME were incubated together for 45 minutes at 37° C. and then injected simultaneously, CEME appeared to be completely protective. With a challenge dose of 10 µg or *E. coli* 0111:B4 LPS, 100% of control mice (i.e., no cationic peptide) were killed. When 50, 100, and 200 µg of CEME were given to mice, 37%, 40% and 45% survival (i.e., 63%, 60% and 55% mortality) respectively was recorded (TABLE 8, FIG. 16). Consistent with its improved ability to bind LPS, CEMA was more protective resulting in 60%, 75%, and 78% survival when given to mice at doses of 50 µg, 100 µg, and 200 µg respectively. To demonstrate that this was associated with a reduction in TNF levels, 10 µg of LPS and 20 mg of Dgal were injected at time 0. Thirty minutes later, the mice were sacrificed and the blood was taken and centrifuged to separate the serum which was used in the cell cytotoxic L929 assay. Results showed the blood levels of TNF ranged from 69–262 U/ml. Mice injected with 200 µg CEMA along with LPS and Dgal showed blood levels of TNF to be 11–16 U/ml at 30 minutes (the CEMA results were comparable to control mice not injected with anything). Such suppression of TNF levels in the animals injected with Dgal, CEMA, and LPS was maintained for up to 2 hours. These results suggest that CEME and, particularly, CEMA have potential in therapy against endotoxin-associated disorders.

TABLE 8

IN VIVO PROTECTION AGAINST ENDOTOXEMIA

| LPS | CEMA | CEME | dead/total | % Mortality |
|---|---|---|---|---|
| 10 ug | 0 | 0 | 5/5 | 100 |
| 10 ug | 200 ug | 0 | 2/9 | 22 |
| 10 ug | 100 ug | 0 | 2/8 | 25 |
| 10 ug | 50 ug | 0 | 2/5 | 40 |
| 10 ug | 0 | 200 ug | 6/11 | 55 |
| 20 ug | 0 | 200 ug | 5/7 | 71 |
| 20 ug* | 0 | 200 ug | 0/3 | 0 |
| 10 ug | 0 | 100 ug | 6/10 | 60 |
| 10 ug | 0 | 50 ug | 5/8 | 63 |
| 0 | 200 ug | 0 | 0/5 | 0 |
| 0 | 0 | 200 ug | 0/5 | 0 |

*LPS and CEME were incubated together for 45 minutes at 37° C. before injection

EXAMPLE 8

Antibacterial Activity of Cationic Peptides

CEME and CEMA were able to kill a broad range of Gram-negative bacteria with MICs ranging from 1–16 µg/ml (Table 9). These bacteria included many of the life-threatening gram-negative pathogens associated with septicemia and endotoxic shock. Consistent with these in vitro data, in a neutropenic mouse model, both CEME and CEMA showed an ability to significantly protect animals against an LD$_{90}$ dose of the mouse pathogenic *Pseudomonas aeruginosa* strain M2 (Table 10), under conditions established to mimic the acute-endotoxin therapeutic regime (single dose studies) and with CEMA using a two dose therapeutic procedure.

Bacteria included the Bort strain of *E. coli* (Bortolussi, et al., *Inf. Immun.*, 25:293, 1979) that was originally derived from a case of neonatal meningitis, and which is therefore considered a relevant pathogenic strain to study, and the 0111:B4 strain of *E. coli* (kindly provided by Dr. D. Morrison) which is a standard source of endotoxin. (Kelly, et al., *Inf. Immun.*, 59:4491, 1991). In addition, *P. aeruginosa* PA01 strain H103, *P. aeruginosa* M2, *P. aeruginosa* K799, *Eschericha coli* UB 1005, *Enterobacter cloacae* 218S, *Salmonella typhimurium* MS7953s, *Klebsiella pneumoniae* ATCC 13883, *Xanthomonas maltophilia* ATCC 13637, and *Acinetobacter calcoacetious* 8193 were employed. LPS was obtained from *E. coli* Bort by the technique of Westphal and Jann, (Westphal, et al., *Acad. Press, Inc. NY.*, 5:83) and from *P. aeruginosa* H103 by the method of Darveau and Hancock, (Darveau, et al., *J. Bacteriol*, 155:831, 1993). *E. coli* 0111:B4 LPS was purchased from Sigma.

TABLE 9

Activity of CEME and CEMA against Gram-negative bacteria

| | MIC (ug/ml) | |
|---|---|---|
| Strain | CEME | CEMA |
| *Escherichia coli* UB1005 | 4 | 4 |
| *Escherichia coli* Bort | 6 | 8 |
| *Escherichia coli* 0111:B4 | 4 | 4 |
| *Enterobacter cloacae* 218S | 4 | 4 |
| *Salmonella typhimurium* MS7953s | 4 | 4 |
| *Klebsiella pneumoniae* ATCC 13883 | 8 | 12 |
| *Pseudomonas aeruginosa* H103 | 16 | 8 |
| *Pseudomonas aeruginosa* K799 | 4.8 | 2.8 |
| *Xanthomonas maltophilia* ATCC 13637 | 8 | 12 |
| *Acinetobacter calcoaceticus* 8193 | 2 | 1 |

TABLE 10

Influence of cationic peptides on survival of neutropenic mice challenged intraperitoneally with *P. aeruginosa* strain M2.

| Therapy | Survival (%) | Significance: p value[1] |
|---|---|---|
| No peptide | 2/30 (6.7%) | — |
| CEME | 8/30 (26.7%) | p = 0.04 |
| CEMA | 13/30 (43.3%) | P = 0.0011 |
| CEMA[2] | 11/20 (55.0%) | p = 0.0002 |

[1]Using Fishers exact test
[2]This group was given two injections of CEMA at 2 hours and 12 hours after the addition *P. aeruginosa*

Blockage of TNF induction in the RAW 264.7 macrophage cell line. RAW 264.7 cells induce TNF in cell cultures in response to LPS addition, and thus represent an in vitro model of LPS-mediated TNF induction.

The murine cell line RAW 264.7 was obtained from ATCC, (Rockville, Md.), and maintained and passaged as described previously (Kelly, et al., supra). TNF induction experiments with LPS were performed as described by Kelly, et al. (supra) Briefly, Dulbecco's modified Eagle medium was aspirated from RAW 264.7 cell grown overnight in 24 well tissue culture plates after seeding with 10$^6$ cell per ml per well and replaced with fresh medium. LPS at a final concentration of 100 ng/ml, was incubated with the cells for 6 hr at 37° C. in 5% $CO_2$ prior to a TNF assay. At the same time as LPS addition, or after prescribed intervals, cationic peptides or polymyxin B were added at final concentrations of 2–50 µg/ml. All assays were performed three times with similar results.

To ensure that the cationic peptides were interacting with the LPS rather than the cell lines, 50 µg/ml cationic peptides were added to macrophage cell lines as described above, and after incubation at 37° C. in 5% $CO_2$ for 60 minutes, the supernatant was removed and added to a second well of untreated RAW 264.7 cells. Fresh medium was added to the peptide-treated RAW cells and 100 ng/ml of LPS was then added to both the peptide-treated cells and those reconstituted with supernatant, and these wells assayed for TNF production after 6 hours incubation at 37° C. in 5% $CO_2$.

To examine effects on whole bacterium induction of TNF, bacteria, grown in Luria broth overnight (approximately $1\times10^8$/ml) and diluted to $10^7\times10^5$ organisms per ml, and RAW 264.7 cells were each added to separate compartments of a transwell diffusion chamber, which contained a 0.2 µm membrane filter separating the two compartments. Peptides were added, when appropriate, to the bacterium-containing compartment at a final concentration of 20 µg/ml. TNF levels were measured after 6 hours of incubation at 37° C. in 5% $CO_2$. All assays were performed three times with similar results.

Control assays were performed to demonstrate that peptides, at the highest concentrations utilized, did not induce TNF, and were not cytotoxic as judged by trypan blue exclusion and continued adherence of RAW 264.7 cells.

TNF was measured in cell culture supernatants and mouse serum on the basis of cytoxicity for L929 fibroblast cell. (Kelly, et al., supra) Periodic controls in which cytotoxicity was neutralized with monoclonal antibodies against TNF-α and TNF-β (Antibodies IP400 and 1221-00; Genzyme Corp., Cambridge, Mass.) indicated that TNF was solely responsible for cytotoxity. TNF activity was expressed in units as the reciprocal of the dilution of TNF that caused 50% cytotoxicity of L929 cells, as computed using the ELISA+program (Meddata, Inc., New York, N.Y.). In our hands one unit of TNF corresponded to 62.5 pg/ml of recombinant murine TNF (Genzyme Corp.).

Control experiments indicated that the cationic peptides were non toxic for this macrophage cell line at the highest concentrations employed in these experiments. Both CEME and CEMA were reproducibly able to inhibit the induction, by E. coli 0111:B4 LPS, of TNF secretion by RAW 264.7 cells (Table 10). As little as 2 µg/ml of peptide reduced TNF induction by more than 50%, whereas 20–50 µg/ml of peptides caused almost complete blockage of TNF induction. Virtually the same results were obtained with E. coli Bort LPS and in preliminary experiments with P. aeruginosa strain H 103 LPS. To demonstrate that this was due to the interaction of the peptides with LPS rather than the macrophages, CEMA at 20 µg/ml was preincubated with RAW 264.7 cell for 60 minutes and then the supernatant removed. Addition of fresh medium and 100 ng/ml of E. coli 0111:B4 LPS led to a very high level of induction of TNF (19062 Units per ml), indicating that the peptides had not represented the ability of the RAW 264.7 to respond to LPS induction. In contrast the supernatants from these preincubations (which presumably contained the peptides) when added to fresh RAW 264.7 cells, were able to suppress the ability of these cells to induce TNF in response to LPS stimulation, producing only 4451 units per ml;.

The kinetics of blocking of TNF induction by CEMA at 20 µg/ml, were also examined and compared to blocking by polymyxin B. Polymyxin B has been demonstrated to have a very high affinity for binding to LPS (Piers, et al., *Mol Micro*, 12(6):951, 1994; Piers, et al., *Antimicrob. Agents, Chemother*, 38(10):2311, 1994; Moore, R. A., *Antimicrob. Agents. Chemother.*, 29:496, 1986) and an ability to block many of the biological activities of LPS (Stokes, et al., *J. Inf. Dis.*, 160:52, 1989; Hanasawa, et al., *Surg. Gynacol. Obster.*, 168:323, 1989). Previous data indicated that CEMA has a very similar and high affinity for LPS, as judged by dansylpolymyxin displacement assays (Piers, K. L., supra, 38(10), 1994). Consistent with this, CEMA was comparable with polymyxin B in its ability to block, by approximately 100% for both, induction of TNF induced by E. coli 0111:B4 and E. coli Bort LPS. Both polymyxin B and CEMA could block LPS induction of TNF by 81% and 99% respectively when added up to 60 minuets after LPS to RAW 264.7 cells.

In man and animal infections, LPS is probably not released as a purified molecule, but rather in association with other bacterial cell components. To mimic this situation, a model system was employed in which the LPS-protein complexes that are naturally released from bacteria were used as a stimulus to induce TNF production in RAW 264.7 cells. Viable cells of E. coli Bort and 0111:B4 or P. aeruginosa H103 were incubated in a transwell filter unit in which a 0.2 µm membrane filter separated the intact bacteria from the compartment containing the RAW 264.7 cells. Control experiments without peptides added, indicated a high level of TNF induction comparable to that shown due to LPS stimulation (Table 11). Addition of 20 µg/ml of peptide to $10^5$, $10^6$, and $10^7$ viable to E. coli 0111:B4 (Table 11) and Bort cells reduced the TNF levels by 90%–96%. Addition of 20 µg/ml of CEMA to $10^6$ viable P. aeruginosa similarly resulted in a 96% reduction of TNF induction.

TABLE 11

Effect of peptides on the production of TNF by the RAW 264.7 macrophage cell line exposed to purified LPS E. coli 0111:B4 LPS or LPS-protein complexes secreted from intact E. coli 0111:B4 cells.
Unit of TNF induced (% of control)[a]

| LPS source | No peptide control[b] | CEME treated | CEMA treated | P × B treated |
|---|---|---|---|---|
| 100 ng purified LPS | 9802 ± 573 | 566 ± 14 (5.8%) | 566 ± 69 (5.8%) | 573 ± 4 (5.8%) |
| $10^5$ viable cells | 12313 ± 999 | 486 ± 40 (3.9%) | 552 ± 61 (4.5%) | ND |
| $10^6$ viable cells | 31438 ± 3299 | 1653 ± 114 (5.3%) | 1892 ± 1370 (6.0%) | ND |
| $10^7$ viable cells | 48176 ± 1411 | 4569 ± 675 (5.9%) | 4126 ± 3890 (8.5%) | ND |

[a]Typical results from 3 separately performed experiments are reported; Results represent the means of two replicates. Cells were treated with 20 µg of peptide or polymyxin B (P × B).
[b]The background TNF produced by the RAW cells alone was 28 ± 2. The TNF produced by CEMA (20 µg) alone was 50 ± 3 units/ml. This was not subtracted from the background.
[c]ND = not done since polymyxin B causes cell lysis

EXAMPLE 9

Blocking of TNF Induction and Lethality Due to LPS Injection into Galactosamine Sensitized Mice Mice are naturally resistant to LPS. Galanos, et al. (Galanos, C., *Proc. Natl. Acad. Sci. USA*, 76:5939, 1979) demonstrated that injection of galactosamine into mice lowers this natural resistance, probably by its action on the liver, rendering mice hypersensitive to amounts of LPS as low as 1 µg or less. Endotoxic shock was induced by intraperitoneal injection of 10 or 20 µg of E. coli 0111:B4 LPS in phosphate-buffered saline (PBS), pH 7.2 into galactosamine-sensitized 8–10 week old female CD-1 mice (Galanos, C., supra; Freudenberg, M. A., *Inf. Immun.*, 51:891, 1986). In experiments involving peptides, 50–200 μg in 100 μl sterile water injected at separate intraperitoneal sites immediately before or after LPS injection. In survival experiments, survival was monitored at 24 to 48 hours post injection. In experiments measuring TNF, blood was withdrawn by cardiac puncture at timed intervals up to 8 hours after the injections and allowed to clot prior to measurement of TNF in the serum.

To measure the anti-bacterial effect of peptides, a similar strategy was employed. Female CD-1 mice were rendered neutropenic with 3 injections of cyclophosphamide as described previously. (Cryz, S. J., *Inf. Immun.*, 39(2): 1067, 1983) An $LD_{900-100}$ dose of *Pseudomonas aeruginosa* strain M2 (approximately $10^2$ organisms per mouse) was injected intra peritoneally and in the single dose experiments, 100 μl of PBS or sterile water containing 200 μg (8.7 mg/kg) of a cationic peptide was injected immediately afterwards. In the two dose experiments, peptide was injected at 1 hour and 14 hours post bacteria. Survival was recorded at 24 and 48 hours.

Figure 17:
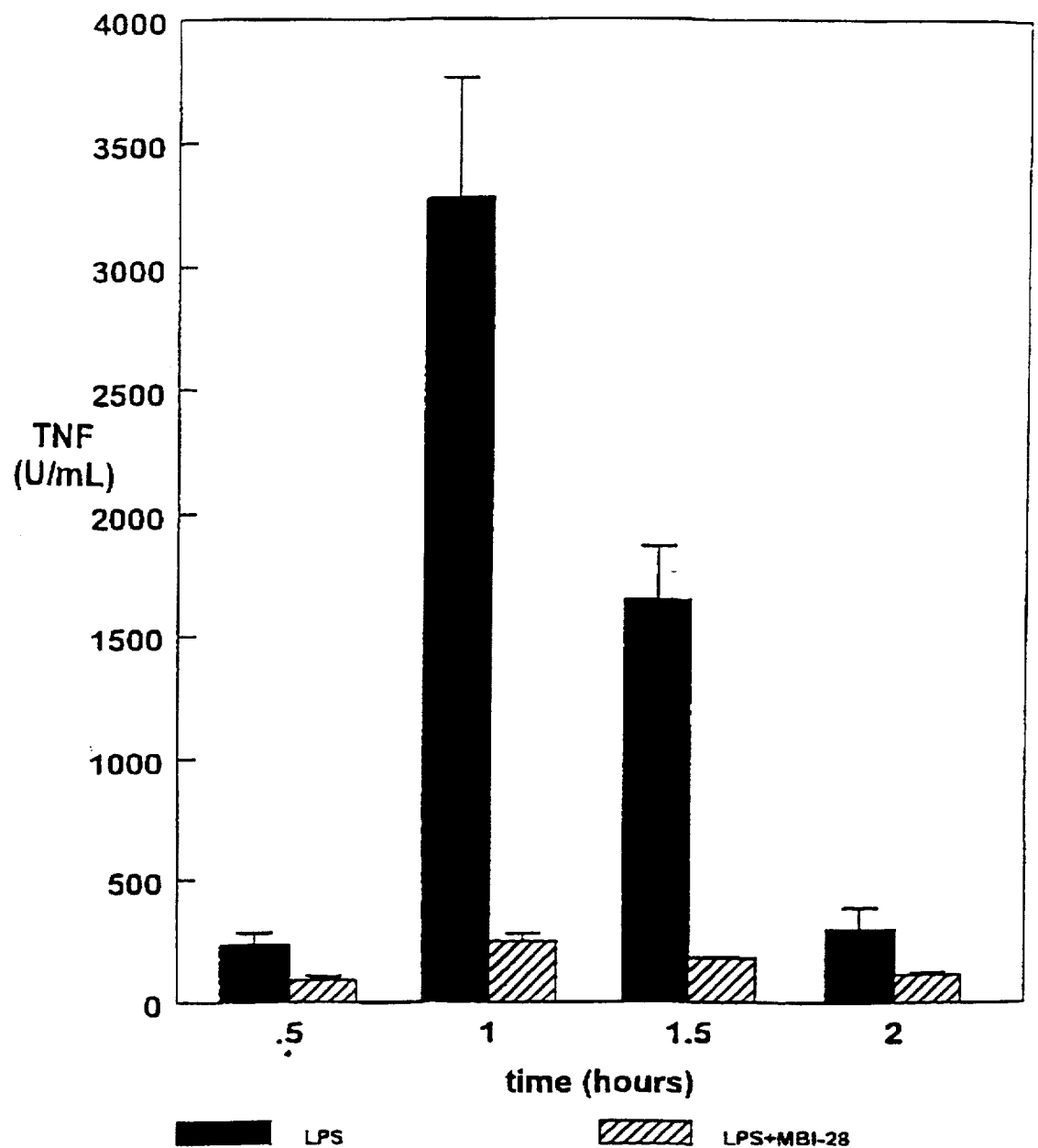
FIG. 17 is a bar graph showing the protective effects of CEME (shown as MBI-27) and CEMA (MBI-28) against lethal endotoxemia in galactosamine-sensitized mice.

A dose of 10–20 μg of LPS injected intra peritoneally caused 100% lethality within 24 hours. In contrast when CEMA was injected at around the same time as LPS, but at separate site in the peritoneum, it protected mice in a dose dependant fashion (FIG. 17). Endotoxemia was induced with 10 μg of *E. coli* 0111:B4 LPS injected into the peritoneum. Subsequently 50, 100, or 200 μg (2.2, 4.4, and 8.7 mg/kg) of CEME or CEMA was injected into a separate site in the peritoneum. Three mice were assessed for each experimental point. Mortality was observed after 24 hrs.

A dose of 200 μg of CEMA (approximately 8.7 mg/kg) protected 78% of mice ($p<0.05$ by Fisher's exact test). Consistent with its lower affinity for LPS, CEME showed a reduced, but also dose-dependant, ability to protect mice against lethal endotoxic shock. Preincubation of CEME with LPS prior to injection resulted in 100% protection, with the difference in protection presumably reflecting the requirement for the peptides to find, bind and neutralize LPS when injected at separate sites in the mouse peritoneum. Control experiments indicated that the peptides themselves did not cause lethality in mice at the highest concentrations utilized here.

Figure 18:
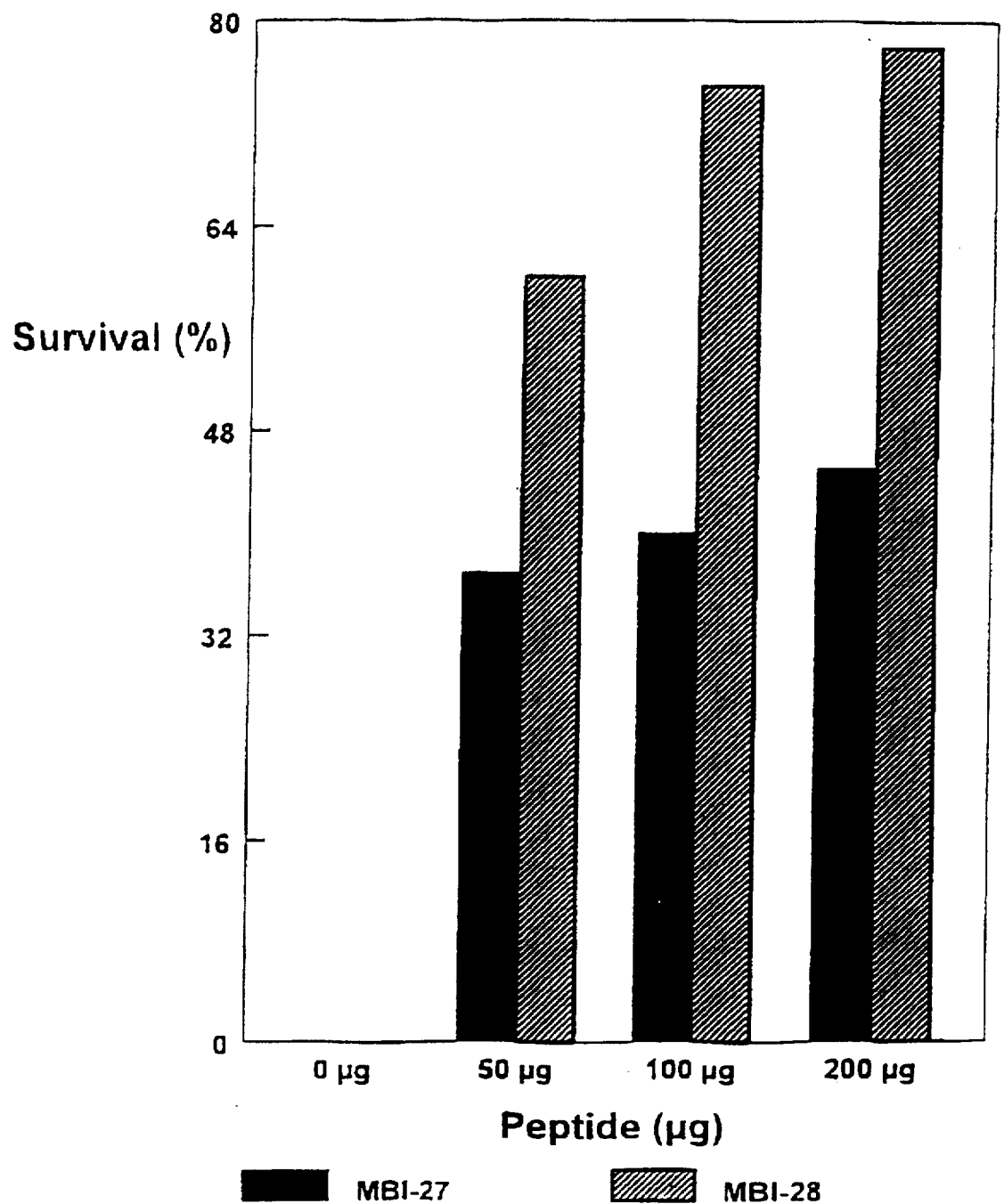
FIG. 18 is a bar graph showing suppression by CEMA of an LPS-induced circulating TNF response in vivo in galactosamine-sensitized mice.

There is a considerable body of evidence that indicates that TNF is a major mediator in endotoxin shock. To examine if the peptides were exerting their effects in animals by suppressing TNF induction, TNF was followed in response to injection of 10 μg of *E. Coli* 0111:B4 into galactosamine treated CD-1 mice. LPS injection led to a typical delayed increase in serum TNF levels that peaked approximately 90 minutes after LPS introduction (FIG. 18). Endotoxemia was induced by intraperitoneal injection of 10 μg of *E. coli* 0111 :B4 LPS and half of the mice also received 200 μg CEMA injected into a separate location in the mouse peritoneum at time zero. At the time points shown, blood was taken and TNF measured in the L929 cytotoxicity assay. Results are presented as the means±standard deviations of TNF levels of mice. However, when 200 μg of CEMA was injected immediately after the LPS a similar kinetics of TNF induction was observed, but serum TNF levels were reduced by 89%.

Although the invention has been described with reference to the presently preferred embodiment, it should be understood that various modifications can be made without departing from the spirit of the invention. Accordingly, the invention is limited only by the following claims.

We claim:

1. A method of inhibiting the growth of bacteria comprising contacting the bacteria with an inhibiting effective amount of the peptide of Sequence ID No.24.

2. The method of claim 1, wherein the bacteria is gram positive.

3. The method of claim 2, wherein the bacteria is *Staphylococcus aureus*.

4. The method of claim 1, wherein the bacteria is gram negative.

5. The method of claim 4, wherein the bacteria is selected from the group consisting of *E. coli, P. aeruginosa, S. typhimurium,* and *E. cloacae*.

6. The method of claim 1, wherein the peptide is administered in combination with at least one antibiotic.

* * * * *